United States Patent
Blesa et al.

(10) Patent No.: US 9,637,728 B2
(45) Date of Patent: May 2, 2017

(54) **VARIANT *TRICHODERMA REESEI* ENDOGLUCANASES**

(71) Applicant: BIOMETHODES, Evry (FR)

(72) Inventors: Stéphane Blesa, Grisy-Suisnes (FR); Céline Coursange, Maisse (FR); Bruno Winter, Cork (IE)

(73) Assignee: BIOMETHODES, Evry (FR)

( * ) Notice: Subject to any disclaimer, the term of this patent is extended or adjusted under 35 U.S.C. 154(b) by 0 days.

(21) Appl. No.: 14/907,663

(22) PCT Filed: Jul. 25, 2014

(86) PCT No.: PCT/EP2014/066106
§ 371 (c)(1),
(2) Date: Jan. 26, 2016

(87) PCT Pub. No.: WO2015/011285
PCT Pub. Date: Jan. 29, 2015

(65) Prior Publication Data
US 2016/0208232 A1 Jul. 21, 2016

(30) Foreign Application Priority Data
Jul. 26, 2013 (EP) .................................... 13306085

(51) Int. Cl.
C12N 9/24 (2006.01)
C12P 19/02 (2006.01)
C12P 19/14 (2006.01)
C12N 9/42 (2006.01)

(52) U.S. Cl.
CPC ......... *C12N 9/2482* (2013.01); *C12N 9/2437* (2013.01); *C12P 19/02* (2013.01); *C12P 19/14* (2013.01); *C12Y 302/01004* (2013.01); *C12P 2203/00* (2013.01); *C12Y 302/01008* (2013.01)

(58) Field of Classification Search
None
See application file for complete search history.

(56) References Cited

FOREIGN PATENT DOCUMENTS

| EP | 0 137 280 | 4/1985 |
|---|---|---|
| JP | H07-51071 | 2/1995 |
| JP | 2009-201425 | 9/2009 |
| WO | WO 2012/036810 | 3/2012 |

OTHER PUBLICATIONS

Written Opinion in International Application No. PCT/EP2014/066106, Sep. 10, 2015, pp. 1-7.

*Primary Examiner* — Christian Fronda
(74) *Attorney, Agent, or Firm* — Saliwanchik, Lloyd & Eisenschenk

(57) ABSTRACT

The present invention provides *T. reesei* endoglucanase I variants exhibiting improved cellulase and/or xylanase activity, in particular at 30° C. and/or pH 6. These variants are particularly useful in industrial processes comprising simultaneous degradation of cellulosic biomass into monomeric sugars and fermentation of said sugars, for example to produce ethanol.

20 Claims, 5 Drawing Sheets

VARIANT *TRICHODERMA REESEI* ENDOGLUCANASES

CROSS-REFERENCE TO RELATED APPLICATION

This application is the U.S. national stage application of International Patent Application No. PCT/EP2014/066106, filed Jul. 25, 2014.

The Sequence Listing for this application is labeled "Seq-List.txt" which was created on Jan. 4, 2016 and is 11 KB. The entire contents of the sequence listing is incorporated herein by reference in its entirety.

FIELD OF THE INVENTION

The present invention relates to the field of biorefinery and more particularly lignocellulosic biomass conversion technologies to produce biofuels, biochemicals and/or biomaterials. The invention relates to endoglucanase variants having improved cellulolytic activity and that are particularly adapted to the needs of simultaneous saccharification and fermentation process.

BACKGROUND OF THE INVENTION

Biomass is a very promising resource for replacing fossil raw materials in applications in which carbon is indispensable, such as liquid fuels, materials and chemicals. However, current technologies are primarily based on the fermentation of sugars derived from starch and sugar crops and thus raise concerns about the diversion of farmlands or crops to biofuels production in detriment of the food supply.

Biorefinery offers the potential to use a wide variety of non-food biomass resources such as agricultural residues, forestry and municipal wastes or dedicated crops such as switchgrass or *miscanthus*, to produce valuable biochemicals, biomaterials and biofuels. Production from this lignocellulosic biomass is thus an attractive alternative that does not interfere with food security.

Biorefinery is based on the conversion of lignocellulosic biomass into monomeric sugars that can be chemically transformed or fermented into various compounds such as biofuels (e.g. bio-ethanol, butanol) or biochemicals (e.g. plastics, detergents, vitamines).

However, one barrier to biorefinery is that the sugars are trapped inside the lignocellulose composed of cellulose, hemicellulose and lignin. Consequently, lignocellulosic biomass has to be pretreated to break down the shield formed by lignin and hemicellulose and disrupt the crystalline structure of cellulose to access the polymer chains. This pretreatment may include physical, chemical and/or biological methods. Cellulose and hemicellulose polymers are then enzymatically or chemically hydrolyzed into monomeric sugars.

Enzymatic hydrolysis of these polymers may be carried out by cellulolytic and hemicellulolytic enzymes. In particular, the enzymatic degradation of cellulose involves synergistic actions of three major classes of enzymes endoglucanases (EG, EC 3.2.1.4), cellobiohydrolases (CBH, EC 3.2.1.91) and beta-glucosidases (BG, EC 3.2.1.21). Indeed, cellobiohydrolases processively cleave cellulose chains at the ends to release soluble cellobiose or glucose, endoglucanases randomly hydrolyze accessible intramolecular β-1,4-glycosidic bonds of cellulose chains to produce new chain ends and beta-glucosidases hydrolyze cellobiose to glucose. Since hemicellulose comprised different sugar monomers such as xylose, mannose or arabinose, the hemicellulytic enzymes are more complex and may involve, for instance, xylanases and mannases.

Currently, many important commercial enzyme preparations for biomass conversion of cellulose or hemicellulose are from the fungus *Trichoderma reesei* (also named *Hypocrea jecorina*) that secretes, for instance, cellobiohydrolases (CBH I and CBH II) and several endoglucanases (e.g. EGI, EGII or EGIII) and beta-glucosidases (e.g. BG I).

Enzymatic hydrolysis and fermentation may be conducted separately. This process is termed process SHF for "Separate enzymatic hydrolysis and fermentation". In this case, pretreated lignocellulosic biomass is enzymatically hydrolysed to monomeric sugars and subsequently fermented in separate units. The advantage of SHF is the ability to carry out each step under optimal conditions, i.e. enzymatic hydrolysis at 45-50° C. and fermentation at about 30° C.

Enzymatic hydrolysis and fermentation may also be conducted simultaneously in the same bioreactor. This process is termed process SSF for "Simultaneous saccharification and fermentation". In this case, sugars produced by the hydrolysing enzymes are consumed immediately by the fermenting microorganism present in the culture. This process is preferred with respect to process integration and simplification but it is less efficient than SHF. Indeed, the main problem for SSF process is that optimum conditions for the enzymatic hydrolysis and fermentation have to be as close as possible. However, the optimum temperatures and pH of cellulases are usually reported to be in the range of 45 to 55° C. and pH 4 to 5 and the optimum temperatures and pH for the most frequently used microorganism for fermenting ethanol in industrial process, i.e. *Saccharomyces cerevisiae*, are about 30° C. and pH 6. The SSF is thus usually performed at about 38° C., which is a compromise between the optimal conditions for hydrolysis and fermentation. However, this made the SSF process much slower (Hari Krishna et al., 2000; Saha et al., 2005).

In order to improve SSF and increase ethanol productivity, thermotolerant yeasts have been developed such as *Kluyveromyces marxianus* (Ballesteros et al., 2004) or *Candida acidothermophilum* (Kadam et al., 1997). Because degradation of cellulose at elevated temperature provides many benefits, such as increased cellulase activity, less energy cost for cooling, and decreased risk of contamination, thermostable cellulases have also been developed and may be advantageously used in combination with these thermotolerant yeasts (Hong et al., 2007). As illustration, thermostable *T. reesei* endoglucanase I variants having substitution at position 230, 113 or 115 of the mature protein, have been disclosed in the patent application WO 2012/036810.

In an alternative approach, enzymatic hydrolysis and fermentation may be carried out by a single community of microorganisms. This process is termed process CBP for "Consolidated Bioprocessing". For this process, ethanol producers can be modified to become cellulase producers or vice-versa. For example, a strain of *Saccharomyces* was modified to express endoglucanase and beta glucosidase (Den Haan et al., 2007). This strain was thus able to grow on cellulose and to converts cellulose to ethanol in one step. However, to date, yields of this process remains insufficient.

Thus, even if much valuable work has been performed during recent years, improvements remain necessary to make biorefinery, and in particular bio fuel production process, economically feasible. In particular, it would be of great interest to increase the productivity and reduce the production cost of processes wherein saccharification and fermentation are conducted simultaneously.

SUMMARY OF THE INVENTION

The invention aims to provide variants of *Trichoderma reesei* endoglucanase I exhibiting increased cellulase and xylanase activities, in particular under conditions that are optimal for fermentation, i.e. at 30° C. and pH 6. These variants are particularly useful in processes wherein saccharification and fermentation are conducted simultaneously, such as SSF and CBP processes, since they allow conducting enzymatic hydrolysis of cellulosic biomass and fermentation of produced sugars at the optimum temperature for fermenting yeasts while preserving the rate and yield of hydrolysis.

Thus, in a first aspect, the present invention relates to an endoglucanase I variant comprising a sequence (i) having at least 96% identity to the full length amino acid sequence set forth in SEQ ID NO: 3 and (ii) comprising at least one substitution at position corresponding to residue E117, D241, T7 or M91 of SEQ ID NO: 3, wherein said variant exhibits an improved cellulase and/or xylanase activity compared to *Trichoderma reesei* endoglucanase I of SEQ ID NO: 2.

The variant may comprise at least two substitutions at positions corresponding to residues selected from the group consisting of E117, D241, T7 and M91 of SEQ ID NO: 3. Preferably, it comprises substitutions at positions corresponding to residues E117 and D241. The variant may also comprise at least three substitutions at positions corresponding to residues selected from the group consisting of E117, D241, T7 and M91 of SEQ ID NO: 3. Preferably, the variant comprises substitutions at positions corresponding to residues E117, D241, T7 and M91 of SEQ ID NO: 3.

The variant may comprise one or several substitutions selected from the group consisting of E117K, D241G, T7I and M91L. In a preferred embodiment, the variant comprises substitutions at positions corresponding to residues E117, D241, T7 and M91 of SEQ ID NO: 3 and said substitutions are E117K, D241G, T7I and M91L.

The variant may comprise a carbohydrate-binding module (CBM) domain linked to the catalytic core of the enzyme. Preferably, the variant lacks carbohydrate-binding module (CBM) domain.

In a second aspect, the present invention relates to a nucleic acid encoding an endoglucanase I variant of the invention. The present invention also relates to an expression cassette or an expression vector comprising said nucleic acid, and to a host cell comprising said nucleic acid, expression cassette or vector.

In a further aspect, the present invention relates to a method of producing an endoglucanase I variant of the invention comprising:

(a) culturing the host cell as defined above in a suitable culture medium under suitable conditions to produce the endoglucanase I variant; and (b) recovering said variant from the cell culture.

Said variant may be recovered, for example, from the supernatant of the cell culture.

In another aspect, the present invention relates to a method of converting cellulosic biomass to monomeric sugars comprising contacting the biomass with an endoglucanase I variant of the invention or a host cell producing said variant.

The present invention also relates to a method of producing a fermentation product from cellulosic biomass comprising (a) contacting the biomass with an endoglucanase I variant of the invention or a host cell producing said variant, thereby degrading the biomass into monomeric sugars; and (b) fermenting monomeric sugars obtained in step (a) into said fermentation product.

In a particular embodiment, steps (a) and (b) are conducted at the same temperature and/or the same pH, preferably at 30° C. and/or pH 6.

DETAILED DESCRIPTION OF THE INVENTION

Figure 1:
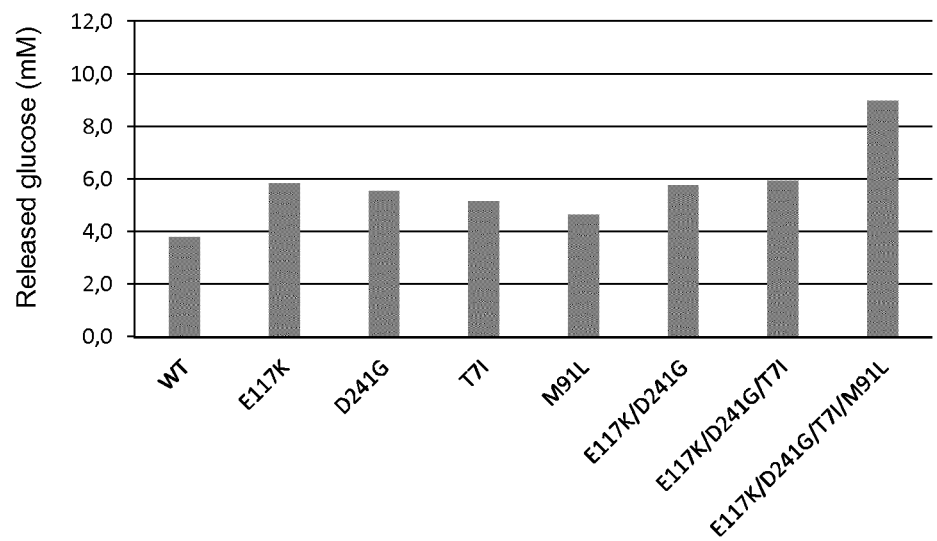
FIG. 1: Cellulase activity on PASC at 30° C. pH 6 of wild-type *T. reesei* endoglucanase I and endoglucanase variants according to the invention (E117K, D241G, T7I, M91L, E117K+D241G, E117K+D241G+T7I and E117K+D241G+T7I+M91L). Released glucose was quantified at t=24 h.

The filamentous fungus *Trichoderma reesei* (teleomorph *Hypocrea jecorina*, Kuhls et al. 1996) is an industrially used cellulolytic organism. Indeed, this fungus is able to produce large quantities of enzymes that constitute a complete cellulase system capable of degrading amorphous as well as crystalline forms of cellulose. The cellulolytic system of *T. reesei* is composed of two cellobiohydrolases (CBHI and CBHII), at least five endoglucanases (EGI, EGII, EGIII, EGIV and EGV) and two β-glucosidases (BGI and BGII).

Endoglucanases (EC 3.2.1.4) belong to the glycosyl hydrolase 7 family and hydrolyze accessible intramolecular β-1,4-glycosidic bonds of cellulose chains. They consist of a catalytic core domain and a carbohydrate-binding module (CBM) domain separated by a flexible linker region. The CBM domain promotes adsorption of the enzyme to regions of the cellulosic substrate, while the core domain is responsible for catalyzing the cleavage of cellulose.

Endoglucanase I (EG-I or CEL7B, Swiss-Prot accession number: P07981) is the major endoglucanase produced by *T. reesei*, accounting for 5 to 10% of the total amount of cellulase produced by this organism. EG-I exhibits both cellulase and xylanase activities. This enzyme is coded by the gene egl1 (GeneBank accession number: M15665). This gene comprises three exons coding a polypeptide chain of 459 amino acids (aa) (SEQ ID NO: 1) comprising a 437-aa long EG-I protein with a 22-aa long signal peptide. The 437-aa long mature protein (SEQ ID NO: 2) comprises a 375-aa long catalytic core domain (SEQ ID NO: 3), a 26-aa long peptide linker and a 37-aa long C-terminal CBM domain.

With the aim to improve the activity of EG-I in conditions where cellulose or hemicellulose hydrolysis and fermentation can be run simultaneously, the inventors have developed novel EG-I variants. They have thus found that the substitution of one or more amino acid residues selected from the group consisting of E117, D241, T7 or M91 of SEQ ID NO: 3, leads to endoglucanase variants having increased cellulase and/or xylanase activities, in particular at 30° C. and/or pH6.

DEFINITIONS

Herein, the terms "peptide", "oligopeptide", "polypeptide" and "protein" are employed interchangeably and refer to a chain of amino acids linked by peptide bonds, regardless of the number of amino acids forming said chain.

The term "wild-type protein" as used herein, refers to the non-mutated version of a polypeptide as it appears naturally in a species. As used herein, the term "wild-type *T. reesei* EG-I" refers to the endoglucanase I of SEQ ID NO: 2.

The amino acids are herein represented by their one-letter or three-letter code according to the following nomenclature: A: alanine (Ala); C: cysteine (Cys); D: aspartic acid (Asp); E: glutamic acid (Glu); F: phenylalanine (Phe); G: glycine (Gly); H: histidine (His); I: isoleucine (Ile); K: lysine (Lys); L: leucine (Leu); M: methionine (Met); N: asparagine (Asn); P: proline (Pro); Q: glutamine (Gln); R: arginine (Arg); S: serine (Ser); T: threonine (Thr); V: valine (Val); W: tryptophan (Trp) and Y: tyrosine (Tyr).

The term "substitution", as used herein in relation to a position or amino acid, means that the amino acid in the particular position has been replaced by another amino acid or that an amino acid different from the one of the wild-type protein is present. Preferably, the term "substitution" refers to the replacement of an amino acid residue by another selected from the naturally-occurring standard 20 amino acid residues, rare naturally occurring amino acid residues (e.g. hydroxyproline, hydroxylysine, allohydroxylysine, 6-N-methyllysine, N-ethylglycine, N-methylglycine, N-ethylasparagine, allo-isoleucine, N-methylisoleucine, N-methylvaline, pyroglutamine, aminobutyric acid, ornithine), and non-naturally occurring amino acid, often made synthetically, (e.g. norleucine, norvaline and cyclohexyl-alanine). Preferably, the term "substitution" refers to the replacement of an amino acid residue by another selected from the naturally-occurring standard 20 amino acid residues (G, P, A, V, L, I, M, C, F, Y, W, H, K, R, Q, N, E, D, S and T). The sign "+" indicates a combination of substitutions. In the present document, the following terminology is used to designate a substitution: E117K denotes that amino acid residue at position 117 of SEQ ID No. 3 (glutamic acid, E) is changed to a lysine (K). The substitution can be a conservative or non-conservative substitution. Examples of conservative substitutions are within the groups of basic amino acids (arginine, lysine and histidine), acidic amino acids (glutamic acid and aspartic acid), polar amino acids (glutamine and asparagine), hydrophobic amino acids (methionine, leucine, isoleucine and valine), aromatic amino acids (phenylalanine, tryptophan and tyrosine), and small amino acids (glycine, alanine, serine and threonine).

The term "endoglucanase I variant" or "EG-I variant", as used herein, refers to an enzyme which is derived from wild-type *T. reesei* EG-I protein and comprises an alteration, i.e., a substitution, insertion, and/or deletion, at one or more (e.g., several) positions. The term "deletion", used in relation to a position or an amino acid, means that the amino acid in the particular position has been deleted or is absent. The term "insertion", used in relation to a position or amino acid, means that one or more amino acids have been inserted or are present adjacent to and immediately following the amino acid occupying the particular position. The variant may be obtained by various techniques well known in the art. In particular, examples of techniques for altering the DNA sequence encoding the wild-type protein, include, but are not limited to, site-directed mutagenesis, random mutagenesis and synthetic oligonucleotide construction.

As used herein, the term "sequence identity" or "identity" refers to the number (%) of matches (identical amino acid residues) in positions from an alignment of two polypeptide sequences. The sequence identity is determined by comparing the sequences when aligned so as to maximize overlap and identity while minimizing sequence gaps. In particular, sequence identity may be determined using any of a number of mathematical global or local alignment algorithms, depending on the length of the two sequences. Sequences of similar lengths are preferably aligned using a global alignment algorithms (e.g. Needleman and Wunsch algorithm; Needleman and Wunsch, 1970) which aligns the sequences optimally over the entire length, while sequences of substantially different lengths are preferably aligned using a local alignment algorithm (e.g. Smith and Waterman algorithm (Smith and Waterman, 1981) or Altschul algorithm (Altschul et al., 1997; Altschul et al., 2005)). Alignment for purposes of determining percent amino acid sequence identity can be achieved in various ways that are within the skill in the art, for instance, using publicly available computer software available on internet web sites such as http://blast.ncbi.nlm.nih.gov/ or http://www.ebi.ac.uk/Tools/emboss/). Those skilled in the art can determine appropriate parameters for measuring alignment, including any algorithms needed to achieve maximal alignment over the full length of the sequences being compared. For purposes herein, % amino acid sequence identity values refers to values generated using the pair wise sequence alignment program EMBOSS Needle that creates an optimal global alignment of two sequences using the Needleman-Wunsch algorithm, wherein all search parameters are set to default values, i.e. Scoring matrix=BLOSUM62, Gap open=10, Gap extend=0.5, End gap penalty=false, End gap open=10 and End gap extend=0.5.

As used herein, the term "cellulase activity" refers to the hydrolysis of a cellulosic material and, in a preferred embodiment, to endoglucanase activity (EC 3.2.1.4), i.e. the clivage of intramolecular β-1,4-glucosidic bonds. This activity can be measured by any method known by the skilled person. A number of well-known methods are available to assess endoglucanase activity, as reviewed in Zhang et al., 2006. These methods include, but are not limited to, reducing sugar assays including the dinitrosalicyclic acid (DNS) method (Ghose, 1987), the Nelson-Somogyi method (Nelson, 1944), the 2,2'-bicinchroninate (BCA) method (Zhang and Lynd, 2005b), the 4-hydroxybenzoylhydrazine (PAHBAH) method (Lever et al., 1973), and the ferricyanide methods (Kidby and Davidson, 1973); total sugar assays wherein sugars can be measured directly by the phenol-$H_2SO_4$ method (Zhang and Lynd, 2005b) or the anthrone-$H_2SO_4$ method (Roe, 1955); and enzymatic glucose assays wherein glucose can be measured using a kit comprising coupled hexokinase and glucose-6-phosphate dehydrogenase (Zhang and Lynd, 2004a). Substrates containing β-1, 4-glucosidic bonds used to detect this activity may be soluble or insoluble. Examples of soluble substrates include, but are not limited to, CMC, dyed CMC, hydroxyethyl cellulose (HEC), cellodextrins, β-methylumbelliferyl-oligosaccharides and p-nitrophenol-oligosaccharides. Examples of insoluble substrates include, but are not limited to, crystalline cellulose such as cotton, microcrystalline cellulose (Avicel), valonia cellulose or bacterial cellulose; amorphous cellulose such as alkali-swollen cellulose (PASC) or regenerated amorphous cellulose (RAC); Dyed cellulose; and chromogenic and fluorephoric derivatives such as trinitrophenyl-carboxymethylcellulose (TNP-CMC) or fluram-cellulose. For purposes of the present invention and as described in the experimental section, cellulase activity is determined by incubating the endoglucanase I variant in the presence of PASC and in presence of beta-glucosidase. Released sugars are then quantified using any suitable assay, for example the 4-hydroxybenzoylhydrazine (PAHBAH) method. Preferably, the endoglucanase I variant is comprised in the cell culture supernatant which was recovered by centrifugation of the culture. The supernatant may optionally be concentrated or diluted. The assay for cellulase activity may be carried out at different pH and temperatures (e.g. pH 4 to 6 and 30 to 60° C.) and for different times (from 30 min to 24 h). Preferably, the assay is carried out at 50° C. pH 5 or 30° C. pH 6.

As used herein, the term "xylanase activity" refers to the endohydrolysis of 1,4-beta-D-xylosidic linkages in xylans (EC 3.2.1.8). As used herein, this activity is the xylanase activity of EG-I or EG-I variant and is distinct from the endo-1,4-beta-xylanase activity of xylanases I (coded by the gene xyn1) and II (coded by the gene xyn2) of *T. reesei* (Swiss-Prot accession numbers P36218 and P36217). Xylanase activity can be measured by determining the reducing sugars formed from various types of xylan, including, for example, oat spelt, beechwood, birch wood and larchwood xylans, or by photometric determination of dyed xylan fragments released from various covalently dyed xylans. For purposes of the present invention and as described in the experimental section, xylanase activity is determined by incubating the endoglucanase I variant in the presence of xylan from beechwood. Released sugars are then quantified using any suitable assay, for example the 4-hydroxybenzoylhydrazine (PAHBAH) method. Preferably, the endoglucanase I variant is comprised in the cell culture supernatant which was recovered by centrifugation of the culture. The supernatant may optionally be concentrated or diluted. The assay for xylanase activity may be carried out at different pH and temperatures (e.g. pH 4 to 6 and 30 to 60° C.) and for different times (from 30 min to 24 h). Preferably, the assay is carried out at 50° C. pH 5 or 30° C. pH 6.

The term "expression", as used herein, refers to any step involved in the production of a polypeptide including, but being not limited to, transcription, post-transcriptional modification, translation, post-translational modification, and secretion.

The term "expression cassette" denotes a nucleic acid construct comprising a coding region, i.e. a nucleic acid of the invention, and a regulatory region, i.e. comprising one or more control sequences, operably linked.

As used herein, the term "expression vector" means a DNA or RNA molecule that comprises an expression cassette of the invention. Preferably, the expression vector is a linear or circular double stranded DNA molecule.

The term "operably linked" means a configuration in which a control sequence is placed at an appropriate position relative to a coding sequence, e.g. a nucleic acid of the invention, in such a way that the control sequence directs expression of the coding sequence.

The term "control sequences" means nucleic acid sequences necessary for expression of a polynucleotide encoding a variant of the present invention. Control sequences may be native (i.e., from the *T. reesei* egl1 gene) or heterologous (i.e., from a different gene and/or a different species) to the polynucleotide encoding the variant. Well-known control sequences and currently used by the person skilled in the art will be preferred. Such control sequences include, but are not limited to, a leader, polyadenylation sequence, propeptide sequence, promoter, signal peptide sequence, and transcription terminator. At a minimum, the control sequences include a promoter and a transcription terminator.

The term "cellulosic biomass" refers to any biomass material comprising cellulose, hemicellulose and/or lignocellulose. Cellulosic biomass includes, but is not limited to, plant material, municipal solid waste, and wastepaper. Plant material includes, but is not limited to, *Miscanthus*, energy grass, elephant grass, switchgrass, cord grass, rye grass, reed canary grass, common reed, wheat straw, barley straw, canola straw, oat straw, corn stover, soybean stover, oat hulls, oat spelt, sorghum, rice hulls, sugarcane bagasse, corn fiber, barley, oats, flax, wheat, linseed, citrus pulp, cottonseed, groundnut, rapeseed, sunflower, peas, lupines, palm kernel, coconut, konjac, locust bean gum, gum guar, soy beans, Distillers Dried Grains with Solubles (DDGS), Blue Stem, corncobs, pine, conifer softwood, *eucalyptus*, birchwood, willow, aspen, poplar wood, hybrid poplar, energy cane, short-rotation woody crop, crop residue, yard waste, or any combination thereof. Preferably, the cellulosic biomass is pre-treated before hydrolysis using the variant of the invention. This pretreatment is intended to open the bundles of lignocelluloses in order to access the polymer chains of cellulose and hemicellulose. Pretreatment methods include physical pretreatments (e.g. high pressure steaming, extrusion, pyrolysis or irradiation), physicochemical and chemical pretreatments (e.g. ammonia fiber explosion, treatments with alkaline, acidic, solvent or oxidizing agents) and biological pretreatments (e.g. using Actinomycetes or Fungi) of lignocellulosic biomass are well known. In some embodiments, the term "cellulosic biomass" may also encompass cellulosic substrates, i.e. partially or totally purified cellulose or hemicellulose. These cellulosic substrates include, but are not limited to, microcrystalline cellulose (Avicel), carboxymethylcellulose (CMC), hydroxyethylcellulose, cotton or amorphous cellulose (phosphoric acid swollen cellulose (PASC) or regenerated amorphous cellulose (RAC)).

In a first aspect, the present invention concerns a variant of *T. reesei* endoglucanase I comprising, or consisting of, a sequence (i) having at least 96% identity to the full length amino acid sequence set forth in SEQ ID NO: 3 and (ii) comprising at least one substitution at position corresponding to residue E117, D241, T7 or M91 of SEQ ID NO: 3.

In an embodiment, the variant of the invention comprises, or consists of, a sequence having at least 96.5%, at least 97%, at least 97.5%, at least 98%, at least 98.5% or at least 99% sequence identity to the full length amino acid sequence set forth in SEQ ID NO: 3. In another embodiment, the variant of the invention comprises, or consists of, a sequence that differs from the sequence set forth in SEQ ID NO:3 by only one, two, three or four substitutions selected from the group consisting of substitutions at positions corresponding to residues E117, D241, T7 and M91 of SEQ ID NO: 3.

In an embodiment, the sequence comprises one substitution at position corresponding to residue E117, D241, T7 or M91 of SEQ ID NO: 3.

In a particular embodiment, the substitution is at position corresponding to residue E117. Preferably, the substitution is selected from the group consisting of E117K, E117R and E117H. More preferably, the substitution is E117K.

In another particular embodiment, the substitution is at position corresponding to residue D241. Preferably, the substitution is selected from the group consisting of D241G, D241A, D241S, D241T and D241R. More preferably, the substitution is selected from the group consisting of D241G and D241R. Even more preferably, the substitution is D241G.

In another particular embodiment, the substitution is at position corresponding to residue T7. Preferably, the substitution is selected from the group consisting of T7I, T7L, T7M, T7Q, T7G and T7V. More preferably, the substitution is selected from the group consisting of T7I, T7L, T7Q, T7G and T7V. Even more preferably, the substitution is T7I.

In a further particular embodiment, the substitution is at position corresponding to residue M91. Preferably, the substitution is selected from the group consisting of M91L, M91I and M91V. More preferably, the substitution is M91L.

In another embodiment, the sequence comprises two substitutions at positions corresponding to residues selected from the group consisting of E117, D241, T7 or M91 of SEQ ID NO: 3. The sequence may thus comprise a combination of two substitutions selected from the group consisting of E117+D241, E117+T7, E117+M91, D241+T7, D241+M91 or T7+M91. The substitution at the position corresponding to residue E117 may be E117K, E117R or E117H, preferably E117K. The substitution at the position corresponding to residue D241 may be D241G, D241A, D241S, D241T or D241R, preferably D241G or D241R, even more preferably D241G. The substitution at the position corresponding to residue T7 may be T7I, T7L, T7M, T7Q, T7G or T7V, preferably T7I, T7L, T7Q, T7G or T7V, even more preferably T7I. The substitution at the position corresponding to residue M91 may be M91L, M91I or M91V, preferably M91L. In a particular embodiment, the sequence comprises a combination of two substitutions selected from the group consisting of E117K+D241G, E117K+D241R, E117K+T7I, E117K+T7V, E117K+T7Q, E117K+T7G, E117K+T7L, E117K+M91L, D241G+T7I, D241G+T7V, D241G+T7Q, D241G+T7G, D241G+T7L, D241R+T7I, D241R+T7V, D241R+T7Q, D241R+T7G, D241R+T7L, D241G+M91L, D241R+M91L, T7I+M91L, T7V+M91L, T7Q+M91L, T7G+M91L and T7L+M91L. In a preferred embodiment, the sequence comprises a combination of two substitutions selected from the group consisting of E117K+D241G, E117K+T7I, E117K+M91L, D241G+T7I, D241G+M91L or T7I+M91L.

In a further embodiment, the sequence comprises three substitutions at positions corresponding to residues selected from the group consisting of E117, D241, T7 or M91 of SEQ ID NO: 3. The sequence may thus comprise a combination of three substitutions selected from the group consisting of E117+D241+T7, E117+D241+M91, E117+T7+M91 and D241+T7+M91. The substitution at the position corresponding to residue E117 may be E117K, E117R or E117H, preferably E117K. The substitution at the position corresponding to residue D241 may be D241G, D241A, D241S, D241T or D241R, preferably D241G or D241R, even more preferably D241G. The substitution at the position corresponding to residue T7 may be T7I, T7L, T7M, T7Q, T7G or T7V, preferably T7I, T7L, T7Q, T7G or T7V, even more preferably T7I. The substitution at the position corresponding to residue M91 may be M91L, M91I or M91V, preferably M91L. In a particular embodiment, the sequence comprises a combination of three substitutions selected from the group consisting of E117K+D241G+T7I, E117K+D241G+T7V, E117K+D241G+T7Q, E117K+D241G+T7G, E117K+D241G+T7L, E117K+D241R+T7I, E117K+D241R+T7V, E117K+D241R+T7Q, E117K+D241R+T7G, E117K+D241R+T7L, E117K+D241G+M91L, E117K+D241R+M91L, E117K+T7I+M91L, E117K+T7V+M91L, E117K+T7Q+M91L, E117K+T7G+M91L, E117K+T7L+M91L, D241G+T7I+M91L, D241G+T7V+M91L, D241G+T7Q+M91L, D241G+T7G+M91L, D241G+T7L+M91L, D241R+T7I+M91L, D241R+T7V+M91L, D241R+T7Q+M91L, D241R+T7G+M91L and D241R+T7L+M91L. In a preferred embodiment, the sequence comprises a combination of three substitutions selected from the group consisting of E117K+D241G+T7I, E117K+D241G+M91L, E117K+T7I+M91L and D241G+T7I+M91L.

In a further embodiment, the sequence comprises substitutions at positions corresponding to residues E117, D241, T7 and M91 of SEQ ID NO: 3. The substitution at the position corresponding to residue E117 may be E117K, E117R or E117H, preferably E117K. The substitution at the position corresponding to residue D241 may be D241G, D241A, D241S, D241T or D241R, preferably D241G or D241R, even more preferably D241G. The substitution at the position corresponding to residue T7 may be T7I, T7L, T7M, T7Q, T7G or T7V, preferably T7I, T7L, T7Q, T7G or T7V, even more preferably T7I. The substitution at the position corresponding to residue M91 may be M91L, M91I or M91V, preferably M91L. In a particular embodiment, the sequence comprises a combination of four substitutions selected from the group consisting of E117K+D241G+T7I+M91L, E117K+D241G+T7V+M91L, E117K+D241G+T7Q+M91L, E117K+D241G+T7G+M91L, E117K+D241G+T7L+M91L, E117K+D241R+T7I+M91L, E117K+D241R+T7V+M91L, E117K+D241R+T7Q+M91L, E117K+D241R+T7G+M91L and E117K+D241R+T7L+M91L. In a preferred embodiment, the sequence comprises the following substitutions: E117K, D241G, T7I and M91L.

In a particular embodiment, the variant comprises, or consists of, a sequence that differs from the sequence set forth in SEQ ID No. 3 by 1, 2, 3, 4, 5, 6, 7, 8, 9, 10, 11, 12, 13, 14 or 15 substitutions, insertions and/or deletions, preferably by 1, 2, 3, 4, 5, 6, 7, 8, 9 or 10 substitutions, insertions and/or deletions, more preferably by 1, 2, 3, 4, 5 substitutions, insertions and/or deletions. In a preferred embodiment, the variant comprises, or consists of, a sequence that differs from the sequence set forth in SEQ ID No. 3 by 1, 2, 3, 4, 5, 6, 7, 8, 9, 10, 11, 12, 13, 14 or 15 substitutions, preferably by 1, 2, 3, 4, 5, 6, 7, 8, 9 or 10 substitutions, more preferably by 1, 2, 3, 4, 5 substitutions.

In an embodiment, the variant of the invention comprises a CBM domain. This CBM domain may be from *T. reesei* EG-I or from any other enzyme comprising a CBM domain. The CBM domain may belong to the Carbohydrate-Binding Module Family 1 as defined on the Carbohydrate-Active enZYmes Database (http://www.cazy.org/CBM1_eukaryota.html). Preferably, the CBM domain is from a fungal cellulase, preferably selected from the group consisting of endoglucanase II (gene egl2) from *Trichoderma reesei*, endoglucanase V (gene egl5) from *Trichoderma reesei*, exocellobiohydrolase I (gene CBHI) from *Humicola grisea, Neurospora crassa, Phanerochaete chrysosporium, Trichoderma reesei* or *Trichoderma viride*, exocellobiohydrolase II (gene CBHII) from *Trichoderma reesei*, exocellobiohydrolase II (gene cel3) from *Agaricus bisporus* or endoglucanases B, F and K from *Fusarium oxysporum*. In a preferred embodiment, the CBM is the CBM domain of the *T. reesei* EG-I. In particular, this CBM may comprise, or consist of, the sequence from residue 401 to residue 437 of SEQ ID NO: 2. The CBM domain may be linked to the C-terminus or the N-terminus of the catalytic core domain, preferably to the C-terminus. Preferably, the CBM domain is linked to the catalytic core though a peptide linker. Usually, this linker is a region rich in proline and/or hydroxyl-amino-acids. For example, this peptide linker may comprise, or consist of, the sequence from residue 376 to residue 400 of SEQ ID NO: 2.

It has been demonstrated that the peptide linker and CBM domain are not required for the cellulase and xylanase activity (Dienes et al., 2006; Nakazawa et al., 2008). Accordingly, in a particular embodiment, the variant of the invention lacks carbohydrate-binding module (CBM) domain. In this case, the variant may still comprise all or part of the peptide linker. Preferably, the variant lacks a peptide linker and a CBM domain. Such a variant can be obtained, for example, by introducing a STOP codon immediately after the codon encoding the last amino acid of SEQ ID NO: 3. The variant may thus only contain the catalytic core domain.

In some embodiment, the variant of the invention is fused at its N-terminus and/or C-terminus to another polypeptide to create a hybrid polypeptide or fusion polypeptide. Techniques for producing fusion polypeptides are known in the art, and include ligating the coding sequences encoding the variant and the addition region of another polypeptide so that they are in frame and that expression of the fusion polypeptide is under control of the same promoter(s) and terminator. Fusion polypeptides may also be constructed using intein technology in which fusion polypeptides are created post-translationally (Cooper et al., 1993; Dawson et al., 1994). The addition region of the fusion polypeptide can be selected in order to enhance the stability of the enzyme, to promote the secretion (such as a N-terminal hydrophobic signal peptide) of the fusion protein from a cell (such as a bacterial cell or a yeast cell), or to assist in the purification of the fusion protein. More particularly, the additional region can be a tag useful for purification or immobilization of the enzyme. Such a tag is well-known by the person skilled in the art, for instance a His tag (His6), a FLAG tag, a HA tag (epitope derived from the Influenza protein haemagglutinin), a maltose-binding protein (MPB), a MYC tag (epitope derived from the human proto-oncoprotein MYC) or a GST tag (small glutathione-S-transferase). A fusion polypeptide can further comprise a cleavage site for proteases or chemical agents, between the enzyme and the addition region. Upon secretion of the fusion protein, the site is cleaved releasing the two separate polypeptides.

The variant of the invention exhibits an improved cellulase and/or xylanase activity compared to the wild-type *T. reesei* endoglucanase I of SEQ ID NO: 2. In particular, said improvement may be (i) an increased cellulase activity at 30° C. and pH 6 by comparison with the WT enzyme in the same conditions, and/or (ii) an increased xylanase activity at 30° C. and pH 6 by comparison with the WT enzyme in the same conditions, and/or (iii) a cellulase activity at 30° C. and pH 6 which is at least equal to the cellulase activity of the WT enzyme at 50° C. and pH 5, and/or (iv) a xylanase activity at 30° C. and pH 6 which is at least equal to the xylanase activity of the WT enzyme at 50° C. and pH 5, and/or (v) an increased cellulase activity by comparison with the WT enzyme in the same conditions, in particular at 30° C. and pH 6 or 50° C. and pH 5, and/or (vi) an increased xylanase activity by comparison with the WT enzyme in the same conditions, in particular at 30° C. and pH 6 or 50° C. and pH 5.

In a particular embodiment, the variant of the invention exhibits an increased cellulase and/or xylanase activity at 30° C. and pH 6 by comparison with the WT enzyme in the same conditions. Preferably, the variant of the invention exhibits increased cellulase and xylanase activities at 30° C. and pH 6 by comparison with the WT enzyme in the same conditions. This variant is thus particularly adapted for cellulosic biomass conversion processes wherein cellulose or hemicellulose hydrolysis and fermentation are carried out simultaneously.

Optionally, the variant may also exhibit increased thermostability as compared to the WT enzyme, in particular between 50° C. and 60° C. This thermostability may be assessed by measuring the cellulase and/or xylanase activity of the variant and/or the WT enzyme after incubation at about 50 to about 60° C. for about one hour.

The present invention also relates to a nucleic acid encoding a variant of the invention. The nucleic acid can be DNA (cDNA or gDNA), RNA, or a mixture of the two. It can be in single stranded form or in duplex form or a mixture of the two. It can comprise modified nucleotides, comprising for example a modified bond, a modified purine or pyrimidine base, or a modified sugar. It can be prepared by any method known to one skilled in the art, including chemical synthesis, recombination, and mutagenesis. The nucleic acid according to the invention may be deduced from the sequence of the peptide according to the invention and codon usage may be adapted according to the host cell in which the nucleic acid shall be transcribed. These steps may be carried out according to methods well known to one of skill in the art and some of which are described in the reference manual Sambrook et al. (Sambrook et al., 2001).

The nucleic acid may encode only the catalytic core domain of the variant (corresponding to the catalytic core domain of the wt enzyme set forth in SEQ ID NO:3), the catalytic core domain associated with a CBM domain and optionally a peptide linker (corresponding to the mature wt enzyme set forth in SEQ ID NO:2), or a precursor form of the variant comprising a signal peptide, preferably promoting the secretion, and the catalytic core domain, optionally associated with a peptide linker and CBM domain (corresponding to the precursor form of the wt enzyme set forth in SEQ ID NO:1).

The present invention further relates to an expression cassette comprising a nucleic acid according to the invention operably linked to one or more control sequences that direct the expression of said nucleic acid in a suitable host cell under conditions compatible with the control sequences.

The control sequence may include a promoter that is recognized by a host cell or an in vitro expression system for expression of a nucleic acid encoding a variant of the present invention. The promoter contains transcriptional control sequences that mediate the expression of the enzyme. The promoter may be any polynucleotide that shows transcriptional activity in the host cell including mutant, truncated, and hybrid promoters, and may be obtained from genes encoding extracellular or intracellular polypeptides either homologous or heterologous to the host cell. Examples of suitable promoters in a bacterial host cell are the promoters obtained from the *Bacillus amyloliquefaciens* alpha-amylase gene (amyQ), *Bacillus licheniformis* alpha-amylase gene (amyL), *Bacillus licheniformis* penicillinase gene (penP), *Bacillus stearothermophilus* maltogenic amylase gene (amyM), *Bacillus subtilis* levansucrase gene (sacB), *Bacillus subtilis* xylA and xylB genes, *Bacillus thuringiensis* cryl11A gene (Agaisse and Lereclus, 1994), *E. coli* lac operon, *E. coli* trc promoter (Egon et al., 1988), *Streptomyces coelicolor* agarase gene (dagA), and prokaryotic beta-lactamase gene (Villa-Kamaroff et al., 1978), as well as the tac promoter (DeBoer et al., 1983). Further promoters are described in "Useful proteins from recombinant bacteria" in Gilbert et al., 1980, and in Sambrook et al., 2001. Examples of tandem promoters are disclosed in WO 99/43835. Examples of suitable promoters in a filamentous fungal host cell are promoters obtained from the genes for *Aspergillus nidulans* acetamidase, *Aspergillus niger* neutral alpha-amylase, *Aspergillus niger* acid stable alpha-amylase, *Aspergillus niger* or *Aspergillus awamori* glucoamylase (glaA), *Aspergillus oryzae* TAKA amylase, *Aspergillus oryzae* alkaline protease, *Aspergillus oryzae* triose phosphate isomerase, *Fusarium oxysporum* trypsin-like protease (WO96/00787), *Fusarium venenatum* amyloglucosidase (WO 00/56900), *Fusarium venenatum* Dania (WO 00/56900), *Fusarium venenatum* Quinn (WO 00/56900), *Rhizomucor miehei* lipase, *Rhizomucor miehei* aspartic proteinase, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase IV, *Trichoderma reesei* endoglucanase V, *Trichoderma reesei* xylanase I, *Trichoderma reesei* xylanase II, *Trichoderma reesei* beta-xylosidase, as well as the NA2-tpi promoter (a modified promoter from an *Aspergillus* neutral alpha-amylase gene in which the untranslated leader has been replaced by an untranslated leader from an *Aspergillus* triose phosphate isomerase gene; non-limiting examples include modified promoters from an *Aspergillus niger* neutral alpha-amylase gene in which the untranslated leader has been replaced by an untranslated leader from an *Aspergillus nidulans* or *Aspergillus oryzae* triose phosphate isomerase gene; and mutant, truncated, and hybrid promoters thereof. In a yeast host, useful promoters are obtained from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH1, ADH2/GAP), *Saccharomyces cerevisiae* triose phosphate isomerase (TPI), *Saccharomyces cerevisiae* metallothionein (CUP1), and *Saccharomyces cerevisiae* 3-phosphoglycerate kinase. Other useful promoters for yeast host cells are described in Romanos et al., 1992.

The control sequence may also be a transcription terminator, which is recognized by a host cell to terminate transcription. The terminator is operably linked to the 3'-terminus of the nucleic acid encoding the variant. Any terminator that is functional in the host cell may be used in the present invention. Preferred terminators for bacterial host cells are obtained from the genes for *Bacillus clausii* alkaline protease (aprH), *Bacillus licheniformis* alpha-amylase (amyL), and *Escherichia coli* ribosomal RNA (rrnB). Preferred terminators for filamentous fungal host cells are obtained from the genes for *Aspergillus nidulans* anthranilate synthase, *Aspergillus niger* glucoamylase, *Aspergillus niger* alpha-glucosidase, *Aspergillus oryzae* TAKA amylase, and *Fusarium oxysporum* trypsin-like protease. Preferred terminators for yeast host cells are obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase. Other useful terminators for yeast host cells are described in Romanos et al., 1992. Usually, the terminator is chosen in correlation with the promoter.

The control sequence may also be an mRNA stabilizer region downstream of a promoter and upstream of the nucleic acid encoding the variant, said mRNA stabilizer region increasing expression of said nucleic acid. Examples of suitable mRNA stabilizer regions are obtained from a *Bacillus thuringiensis* cryl11A gene (WO 94/25612) and a *Bacillus subtilis* SP82 gene (Hue et ai, 1995).

The control sequence may also be a leader, a non-translated region of an mRNA that is important for translation by the host cell. The leader is operably linked to the 5'-terminus of the nucleic acid encoding the variant. Any leader that is functional in the host cell may be used. Preferred leaders for filamentous fungal host cells are obtained from the genes for *Aspergillus oryzae* TAKA amylase and *Aspergillus nidulans* triose phosphate isomerase. Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence operably linked to the 3'-terminus of the nucleic acid encoding the variant and, when transcribed, is recognized by the host cell as a signal to add polyadenosine residues to transcribed mRNA. Any polyadenylation sequence that is functional in the host cell may be used. Preferred polyadenylation sequences for filamentous fungal host cells are obtained from the genes for *Aspergillus nidulans* anthranilate synthase, *Aspergillus niger* glucoamylase, *Aspergillus niger* alpha-glucosidase, *Aspergillus oryzae* TAKA amylase, and *Fusarium oxysporum* trypsin-like protease. Useful polyadenylation sequences for yeast host cells are described by Guo and Sherman, 1995.

The control sequence may also be a signal peptide coding region that encodes a signal peptide linked to the N-terminus of the variant and directs the variant into the cell's secretory pathway, i.e. for secretion into the extracellular (or periplasmic) space. The 5'-end of the coding sequence of the nucleic acid may contain a signal peptide coding sequence naturally linked in translation reading frame with the segment of the coding sequence that encodes the variant. Alternatively, the 5'-end of the coding sequence may contain a signal peptide coding sequence that is foreign to the coding sequence. A foreign signal peptide coding sequence may replace the natural signal peptide coding sequence in order to enhance secretion of the polypeptide. Any signal peptide coding sequence that directs the expressed polypeptide into the secretory pathway of a host cell may be used. Examples of effective signal peptide coding sequences for bacterial host cells include, but are not limited to, the signal peptide coding sequences obtained from the genes for *Bacillus* NCIB 11837 maltogenic amylase, *Bacillus licheniformis* subtilisin, *Bacillus licheniformis* beta-lactamase, *Bacillus stearothermophilus* alpha-amylase, *Bacillus stearothermophilus* neutral proteases (nprT, nprS, nprM), *Bacillus subtilis* prsA, and other signal peptides described by Simonen and Palva, 1993. Examples of effective signal peptide coding sequences for filamentous fungal host cells include, but are not limited to, the signal peptide coding sequences obtained from the genes for *Aspergillus niger* neutral amylase, *Aspergillus niger* glucoamylase, *Aspergillus oryzae* TAKA amylase, *Humicola insolens* cellulase, *Humicola insolens* endoglucanase V, *Humicola lanuginosa* lipase, and *Rhizomucor miehei* aspartic proteinase. Examples of effective signal peptides for yeast host cells include, but are not limited to, the signal peptide coding sequences obtained from the genes for *Saccharomyces cerevisiae* alpha-factor and *Saccharomyces cerevisiae* invertase, and other signal peptide coding sequences described by Romanos et al., 1992. These signal peptide coding sequences can be cleaved by a number of signal peptidases, thus removing them from the rest of the expressed variant.

It may also be desirable to add regulatory sequences that regulate expression of the variant relative to the growth of the host cell. Examples of regulatory systems are those that cause expression of the gene to be turned on or off in response to a chemical or physical stimulus, including the presence of a regulatory compound. Regulatory systems in prokaryotic systems include the lac, tac, and trp operator systems. In yeast, the ADH2 system or GAL1 system may be used. In filamentous fungi, the *Aspergillus niger* glucoamylase promoter, *Aspergillus oryzae* TAKA alpha-amylase promoter, and *Aspergillus oryzae* glucoamylase promoter may be used. Other examples of regulatory sequences are those that allow for gene amplification. In eukaryotic systems, these regulatory sequences include the dihydrofolate reductase gene that is amplified in the presence of methotrexate, and the metallothionein genes that are amplified with heavy metals. In these cases, the polynucleotide encoding the polypeptide would be operably linked with the regulatory sequence.

Typically, the expression cassette comprises, or consists of, a nucleic acid according to the invention operably linked to a transcriptional promoter and a transcription terminator. Preferably, the expression cassette further comprises a signal peptide coding region leading to secretion into the variant into the extracellular space.

The present invention also relates to an expression vector comprising a nucleic acid or an expression cassette according to the invention. Said expression vector may be used to transform a host cell and enable the expression of the nucleic acid of the invention in said cell. The choice of the vector will typically depend on the compatibility of the vector with the host cell into which the vector is to be introduced. The vector may be an autonomously replicating vector, i.e., a vector that exists as an extra-chromosomal entity, the replication of which is independent of chromosomal replication, e.g., a plasmid, an extra-chromosomal element, a mini-chromosome, or an artificial chromosome. The vector may contain any means for assuring self-replication. Alternatively, the vector may be one that, when introduced into the host cell, is integrated into the genome and replicated together with the chromosome(s) into which it has been integrated.

The vector preferably comprises one or more selectable markers that permit easy selection of host cells comprising the vector. A selectable marker is a gene the product of which provides for biocide or viral resistance, resistance to heavy metals, prototrophy to auxotrophy, and the like. Examples of bacterial selectable markers include, but are not limited to, *Bacillus licheniformis* or *Bacillus subtilis* genes or markers that confer antibiotic resistance such as ampicillin, chloramphenicol, kanamycin, neomycin, spectinomycin, or tetracycline resistance. Suitable markers for yeast host cells include, but are not limited to, ADE2, HIS3, LEU2, LYS2, MET3, TRP1, and URA3. Selectable markers for use in a filamentous fungal host cell include, but are not limited to, amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof.

The vector preferably comprises an element that permits integration of the vector into the host cell's genome or autonomous replication of the vector in the cell independent of the genome. When integration into the host cell genome occurs, integration of the sequences into the genome may rely on homologous or non-homologous recombination. In one hand, the vector may contain additional polynucleotides for directing integration by homologous recombination at a precise location into the genome of the host cell. These additional polynucleotides may be any sequence that is homologous with the target sequence in the genome of the host cell. On the other hand, the vector may be integrated into the genome of the host cell by non-homologous recombination.

For autonomous replication, the vector may further comprise an origin of replication enabling the vector to replicate autonomously in the host cell in question. The origin of replication may be any plasmid replicator mediating autonomous replication that functions in a cell. The term "origin of replication" or "plasmid replicator" means a polynucleotide that enables a plasmid or vector to replicate in vivo. Examples of bacterial origins of replication include, but are not limited to, the origins of replication of plasmids pBR322, pUC19, pACYC177, and pACYC184 permitting replication in *E. coli*, and pUB1 10, pE194, pTA1060, and pAMβ1 permitting replication in *Bacillus*. Examples of origins of replication for use in a yeast host cell include, but are not limited to, the 2 micron origin of replication, ARS1, ARS4, the combination of ARS1 and CEN3, and the combination of ARS4 and CEN6. Examples of origins of replication useful in a filamentous fungal cell include, but are not limited to, AMA1 and ANSI (Gems et al., 1991; Cullen et al., 1987).

The methods for selecting these elements according to the host cell in which expression is desired, are well known to one of skill in the art. The vectors may be constructed by the classical techniques of molecular biology, well known to one of skill in the art.

The present invention further relates to the use of a nucleic acid, an expression cassette or an expression vector according to the invention to transform, transfect or transduce a cell. The present invention also relates to a host cell comprising a nucleic acid, a cassette or an expression vector according to the invention.

The host cell may be transformed, transfected or transduced in a transient or stable manner. An expression cassette or vector of the invention is introduced into a host cell so that the cassette or vector is maintained as a chromosomal integrant or as a self-replicating extra-chromosomal vector as described earlier. The term "host cell" also encompasses any progeny of a parent host cell that is not identical to the parent host cell due to mutations that occur during replication. The host cell may be any cell useful in the production of a variant of the present invention, e.g., a prokaryote or a eukaryote.

The prokaryotic host cell may be any Gram-positive or Gram-negative bacterium. Examples of suitable bacterial expression hosts include, but are not limited to, *Escherichia* (e.g. *Escherichia coli*), *Pseudomonas* (e.g. *P. fluorescens* or *P. stutzerei*), *Proteus* (e.g. *Proteus mirabilis*), *Ralstonia* (e.g. *Ralstonia eutropha*), *Streptomyces*, *Staphylococcus* (e.g. *S. carnosus*), *Lactococcus* (e.g. *L. lactis*), or *Bacillus* (*subtilis, megaterium, licheniformis*, etc.).

The host cell may also be an eukaryotic cell, such as a yeast, fungal, mammalian, insect or plant cell. Examples of suitable yeast expression hosts include, but are not limited to, *Saccharomyces* (e.g. *Saccharomyces cerevisiae, Saccharomyces carlsbergensis, Saccharomyces diastaticus, Saccharomyces douglasii, Saccharomyces kluyveri, Saccharomyces norbensis, Saccharomyces oviformis*), *Schizosaccharomyces* (e.g. *Schizosaccharomyces pombe*), *Yarrowia* (e.g. *Yarrowia lipolytica*), *Hansenula* (e.g. *Hansenula polymorpha*), *Kluyveromyces* (e.g. *Kluyveromyces lactis*), *Pichia* (e.g. *Pichia pastoris*) or *Candida* cell.

Especially suited are filamentous fungal host cells. "Filamentous fungi" include all filamentous forms of the subdivision *Eumycota* and *Oomycota* (as defined by Hawksworth et al., 1995). The filamentous fungi are generally characterized by a mycelial wall composed of chitin, cellulose, glucan, chitosan, mannan, and other complex polysaccharides. The filamentous fungal host cell may be a *Trichoderma, Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Schizophyllum, Talaromyces, Thermoascus, Thielavia, Tolypocladium* or *Trametes* cell. For example, the filamentous fungal host cell may be a *Trichoderma reesei, Trichoderma harzianum, Trichoderma koningii, Trichoderma longibrachiatum, Trichoderma viride, Aspergillus awamori, Aspergillus foetidus, Aspergillus fumigatus, Aspergillus japonicus, Aspergillus nidulans, Aspergillus niger, Aspergillus oryzae, Bjerkandera adusta, Ceriporiopsis aneirina, Ceriporiopsis caregiea, Ceriporiopsis gilvescens, Ceriporiopsis pannocinta, Ceriporiopsis rivulosa, Ceriporiopsis subrufa, Ceriporiopsis subvermispora, Chrysosporium inops, Chrysosporium keratinophilum, Chrysosporium lucknowense, Chrysosporium merdarium, Chrysosporium pannicola, Chrysosporium queenslandicum, Chrysosporium tropicum, Chrysosporium zonatum, Coprinus cinereus, Coriolus hirsutus, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola insolens, Humicola lanuginosa, Mucor miehei, Myceliophthora thermophila, Neurospora crassa, Penicillium purpurogenum, Phanerochaete chrysosporium, Phlebia radiata, Pleurotus eryngii, Thielavia terrestris, Trametes villosa*, or *Trametes versicolor* cell.

The nucleic acid, expression cassette or expression vector according to the invention may be introduced into the host cell by any method known by the skilled person, such as electroporation, conjugation, transduction, competent cell transformation, protoplast transformation, protoplast fusion, biolistic "gene gun" transformation, PEG-mediated transformation, lipid-assisted transformation or transfection, chemically mediated transfection, lithium acetate-mediated transformation, liposome-mediated transformation, Optionally, more than one copy of a nucleic acid, cassette or vector of the present invention may be inserted into a host cell to increase production of the variant.

In a particular embodiment, the host cell expresses one or several additional cellulolytic enzymes. These enzymes may be endogenous or heterologous enzymes. These additional enzymes may be, for example, xylanases, endoglucanases, alpha-galactosidases and/or cellobiohydrolases. In another particular embodiment, the host cell is chosen to be able to ferment monomeric sugars and is transformed with a nucleic acid, expression cassette or expression vector according to the invention to obtain a modified strain exhibiting cellulolytic properties. This type of strains is particularly adapted to CBP processes wherein a single microorganism community is used for cellulose or hemicellulose hydrolysis and fermentation.

In another aspect, the present invention relates to a method of producing the endoglucanase I variant of the invention comprising expressing a nucleic acid encoding the variant and recovering the variant.

In particular, the present invention relates to in vitro methods of producing the variant of the present invention comprising (a) contacting a nucleic acid, cassette or vector of the invention with an in vitro expression system; and (b) recovering the variant. In vitro expression systems are well-known by the person skilled in the art and are commercially available.

Preferably, the present invention relates to a method of producing an endoglucanase I variant comprising (a) culturing a host cell according to the invention in a suitable culture medium under suitable conditions to produce endoglucanase I variant; and (b) recovering said variant from the cell culture.

The host cells are cultivated in a nutrient medium suitable for production of polypeptides using methods known in the art. For example, the cell may be cultivated by shake flask cultivation, or small-scale or large-scale fermentation (including continuous, batch, fed-batch, or solid state fermentations) in laboratory or industrial fermentors performed in a suitable medium and under conditions allowing the enzyme to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the variant is secreted into the nutrient medium, the variant can be recovered directly from the culture supernatant. If the variant is not secreted, it can be recovered from cell lysates or after permeabilisation. The variant may be detected using any method known in the art. In particular, the variant may be detected by cellulase or xylanase enzymatic assay (e.g. by contacting the variant with cellulose or xylan as substrate and measuring the quantity of products or the quantity of substrate). The variant may be recovered using any method known in the art. For example, the variant may be recovered from the nutrient medium by conventional procedures including, but not limited to, collection, centrifugation, filtration, extraction, spray-drying, evaporation, or precipitation. Optionally, the variant may be partially or totally purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction to obtain substantially pure polypeptides. In a preferred embodiment, the variant is not recovered before use, but rather a host cell of the present invention expressing the variant is used as a source of the variant and is thus cultured in presence of the cellulosic biomass to be converted.

The present invention also relates to the use of a variant according to the present invention for preparing a variant immobilized on a solid support; and a method for preparing a variant of the invention immobilized on a solid support comprising producing the variant as detailed above and immobilizing the variant on a solid support. The present invention also relates to a solid support, a variant according to the present invention being immobilized on the solid support. Immobilization means are well-known to the person skilled in the art (see e.g. 'Enzyme Technology' by Martin Chaplin and Christopher Bucke, Cambridge University Press, 1990). The variant according to the present disclosure can be immobilized on the solid support by any convenient mean, in particular adsorption, covalent binding, entrapment or membrane confinement. A wide variety of insoluble materials may be used to immobilize the variant. These are usually inert polymeric or inorganic matrices. The solid support can be for instance membranous, particulate or fibrous. More particularly, the solid support is preferably a bead, e.g., micro- or nanobeads. The variant can be immobilized on a polyurethane matrix, on activated sepharose, alginate, amberlite resin, Sephadex resin or Duolite resin. Other solid supports useful for the invention include resins with an acrylic type structure, polystyrene resins, macroreticular resins and resins with basic functional groups. The immobilized variant may then be used in a reactor. Examples of reactor include, but are not limited to, an enzyme reactor, a membrane reactor, a continuous flow reactor such as a stirred tank reactor, a continuously operated packed bed reactor, a continuously operated fluidized bed reactor, and a packed bed reactor.

The present invention also relates to compositions comprising a variant or a host cell of the invention. In an embodiment, the composition comprises a variant of the invention. Preferably, the composition further comprises components suitable for enzyme preservation. The variant may be free or immobilized on a solid support, preferably beads. The composition can be liquid or dry. It comprises the variant according to the invention in a purified or enriched form. In particular, the composition may further comprise stabilisers like glycerol, sorbitol or monopropylene glycol, additives like salts, sugar, preservatives or buffering agents, a redox agent such as DTT (Dithiothreitol), or a sequester such as EDTA (Ethylenediaminetetraacetic acid). In a particular embodiment, the composition is liquid and comprises at least 10, 20, 30, 40 or 50% (w/v), preferably between 20 and 50% (w/v), of glycerol, sorbitol or monopropylene glycol, preferably glycerol. The composition may also further comprise one or more additional proteins of interest. These proteins may be selected, for example, from the group consisting of hemicellulases, alpha-galactosidases, beta-galactosidases, lactases, beta-glucosidases, beta-glucanases, endo-beta-1,4-glucanases, cellulases, xylosidases, xylanases, xyloglucanases, xylan acetyl-esterases, galactanases, endo-mannanases, exo-mannanases, pectinases, pectin lyases, pectinesterases, polygalacturonases, arabinases, rhamnogalacturonases, laccases, reductases, oxidases, phenoloxidases, ligninases, proteases, amylases, phosphatases, lipolytic enzymes and cutinases, and any combinations thereof. In a particular embodiment, the composition is the supernatant of the culture medium used to produce the endoglucanase variant of the invention from host cell. In this embodiment, the variant is secreted into the extracellular space or is released after permeabilisation or lysis of host cells.

In another embodiment, the composition comprises a host cell of the invention. The composition can be liquid (e.g. suspension) or dry (e.g. freeze-dried composition). Preferably, the composition comprising the host cell is kept frozen (e.g. at about −20° C.) until use. Preferably, the composition further comprises components suitable for cell preservation, in particular if cells are frozen. The composition of the invention may comprise one or several host cells of the invention, and optionally one or several additional cells. In particular, additional cells may be cellulolytic microorganisms (e.g. cellulase, xylanase producers) or fermenting microorganisms (e.g. ethanol producers).

The present invention also relates to a kit for hydrolyzing cellulose or hemicellulose comprising a variant of the invention or a host cell of the invention expressing said variant. The kit may further comprise other reagents such as one or several additional enzymes such as hemicellulases, alpha-galactosidases, beta-galactosidases, lactases, beta-glucanases, endo-beta-1,4-glucanases, cellulases, xylosidases, xylanases, xyloglucanases, xylan acetyl-esterases, galactanases, endo-mannanases, exo-mannanases, pectinases, pectin lyases, pectinesterases, polygalacturonases, arabinases, rhamnogalacturonases, laccases, reductases, oxidases, phenoloxidases, ligninases, proteases, amylases, phosphatases, lipolytic enzymes, cutinases, glucuronidase, acetylesterase, xylanase, b-xylosidase, galactomannanase and/or glucomannanase. The kit may also comprise other cells such as cellulolytic microorganisms (e.g. cellulase, xylanase producers) or fermenting microorganisms (e.g. ethanol producers).

The endoglucanase variants, nucleic acids, cassettes, vectors, host cells, and compositions of the present invention may find use in a variety of industrial applications, including in the degradation of cellulosic biomass into monomeric sugars, textile methods (cleaning, cotton softening, denim finishing), in production and uses of detergents (e.g. for color care, cleaning, anti-deposition), for food-based methods (e.g. food processing and mashing), for pulp and paper methods (e.g. paper pulp bleaching, deinking, drainage improvement, production of polished crystalline cellulose, and fiber modification).

The present invention thus further relates to the use of an endoglucanase variant, a composition or a host cell of the invention for converting cellulosic biomass to monomeric sugars, wherein the biomass is contacted with an endoglucanase I variant, a composition or a host cell of the invention. The invention also related to a method of converting cellulosic biomass to monomeric sugars comprising contacting the biomass with an endoglucanase I variant, a composition or a host cell of the invention.

One or several additional enzymes may be used in combination with the endoglucanase variant of the invention such as hemicellulases, alpha-galactosidases, beta-galactosidases, lactases, beta-glucanases, endo-beta-1,4-glucanases, cellulases, xylosidases, xylanases, xyloglucanases, xylan acetyl-esterases, galactanases, endo-mannanases, exo-mannanases, pectinases, pectin lyases, pectinesterases, polygalacturonases, arabinases, rhamnogalacturonases, laccases, reductases, oxidases, phenoloxidases, ligninases, proteases, amylases, phosphatases, lipolytic enzymes, cutinases, glucuronidase, acetylesterase, xylanase, b-xylosidase, galactomannanase and/or glucomannanase.

Monomeric sugars include, but are not limited to, glucose, xylose, mannose, glucuronoxylose, arabinoxylose, glucomannose, and xyloglucose.

In a preferred embodiment, the cellulosic biomass is pretreated before to be contacted with the variant, composition or host cell of the invention. The pretreatment is intended to disorganize the crystalline structure to access the polymer chains of cellulose and hemicellulose and/or modify the pores in the material to allow the enzymes to penetrate into the fibers to render them amenable to enzymatic hydrolysis. Pretreatments may be physical, physicochemical, chemical or biological treatments and are well-known by the skilled person.

In an embodiment, the monomeric sugars obtained are then contacted with a fermenting microorganism to produce a fermentative product, e.g. ethanol.

The present invention further relates the use of an endoglucanase variant, a composition or a host cell of the invention for producing a fermentation product from cellulosic biomass.

The present invention also relates to a method of producing a fermentation product from cellulosic biomass comprising (a) contacting the biomass with an endoglucanase variant, a composition or a host cell of the invention thereby degrading the biomass into monomeric sugars; and (b) fermenting monomeric sugars obtained in step (a) into said fermentation product.

Thanks to the improved cellulase and/or xylanase activity at 30° C. of the endoglucanase variant of the invention, steps (a) and (b) can be conducted at a temperature between 30° C. and 38° C., more preferably between 35° C. and 30° C., and event more preferably about 30° C.

Furthermore, thanks to the improved cellulase and/or xylanase activity at pH 6 of the endoglucanase variant of the invention, steps (a) and (b) can be conducted at a pH between 7 and 5, preferably between 6.5 and 5.5, more preferably about 6.

In a particular embodiment, steps (a) and (b) are conducted at the same temperature and/or the same pH, preferably at the same temperature and the same pH. In a preferred embodiment, steps (a) and (b) are conducted at 30° C. and/or pH 6, preferably at 30° C. and pH 6. Optionally, steps (a) and (b) may be carried out in the same reactor.

In an embodiment, the fermentation is carried out by the host cell of the invention used in step (a).

In another embodiment, the fermentation is carried out by a microorganism different than the host cell of the invention used in step (a).

In an embodiment, step (a), i.e. enzymatic hydrolysis of the cellulosic biomass, is separated from step (b), i.e. fermentation step. In this case, cellulosic biomass is hydrolyzed to monomeric sugars, e.g. glucose, and subsequently fermented to ethanol in separate units.

In a preferred embodiment, step (a) and step (b) are conducted simultaneously in the same reactor. This process may be SSF (Simultaneous Saccharification and Fermentation) or CBP (Consolidated Bioprocessing) process. In such process, monomeric sugars, e.g. glucose, produced by the hydrolyzing enzymes is consumed immediately by the fermenting microorganism present in the culture. For SSF process, this fermenting microorganism is different from the hydrolyzing microorganism used in step (a). For CBP process, steps (a) and (b) are carried out by the same microorganism. Preferably, the method of producing a fermentation product from cellulosic biomass of the invention is a SSF or CBP process.

The fermentation is a metabolic process carried out by a microorganism wherein monomeric sugars are converted to a product. This metabolic pathway may be naturally encoded by the microorganism, or said microorganism may have been genetically engineered to carry out such pathway. Examples of fermentation products include, but are not limited to, biofuel, lactic acid, succinic acid, propanoïc acid, ethanoïc acid, butanoïc acid; propane-1,3-diol, gaseous olefins such as ethylene, propylene, n-butenes, butadiene, isobutylene or isoprene. Preferably, the fermentation product is selected from the group consisting of bio fuel, lactic acid and succinic acid.

Biofuel may be selected from the group consisting of ethanol, butanol, iso-butanol, propanol, 2,5-dimethylfuran, gamma-valerolactone. Preferably, biofuel is ethanol. Ethanol may be used as a fuel additive or extender in blends of from less than 1% and up to 100% (a fuel substitute). The ethanol-producing fermenting microorganism may be any microorganism known in the art that produces ethanol as fermentation product. Specifically, the microorganism may be yeast. More specifically, the yeast may belong to the genus *Saccharomyces, Schizosaccharomyces, Sporobolomyces, Torulopsis, Trichosporon, Wickerhamia, Ashbya, Blastomyces, Candida, Citeromyces, Crebrothecium, Cryptococcus, Debaryomyces, Endomycopsis, Geotrichum, Hansenula, Kloeckera, Lipomyces, Pichia, Rhodosporidium* or *Rhodotorula*. Preferably, the fermenting microorganism belongs to the genus *Saccharomyces*. In a preferred embodiment, the fermenting microorganism is selected from the group consisting of *Saccharomyces cerevisiae, Saccharomyces baynus, Saccharomyces carlsbergensis, Zymomonas mobilis, Clostridium thermocellum, Candida utilis* and *Pichia stipitis*.

Lactic acid is largely used in the food industry and in particular as a food additive, a food preservative, a curing agent, or a flavoring agent. Lactic acid may be obtained by fermentation, for example, using bacteria belonging to the genus *Lactococcus, Lactobacillus, Streptococcus* or *Leuconostoc*. Succinic acid is largely used in the food and beverage industry as an acidity regulator, a food additive or a pharmaceutically acceptable excipient. Succinic acid may be obtained by fermentation using bacteria such as *Actinobacillus succinogenes, Mannheimia succiniproducens* or *Escherichia Coli*.

In a further aspect, the present invention relates to the use of an endoglucanase variant, a composition or a host cell of the invention for increasing the digestibility of plant material by animals. The present invention also relates to a method of increasing the digestibility of plant material by animals comprising contacting the plant material with an endoglucanase variant, a composition or a host cell of the invention thereby increasing the digestibility of said plant material.

Indeed, plant material comprises cellulosic material that greatly reduces the digestibility by animals. In particular, plant material may include palm kernel, coconut, konjac, locust bean gum, gum guar, soy beans, barley, oats, flax, wheat, corn, linseed, citrus pulp, cottonseed, groundnut, rapeseed, sunflower, peas, and/or lupines.

In a further aspect, the present invention relates to the use of an endoglucanase variant, a composition or a host cell of the invention for textile cleaning, cotton softening or denim finishing. The present invention also relates to a method of cleaning textile, softening cotton or finishing denim comprising contacting the textile, cotton or denim with an endoglucanase variant, a composition or a host cell of the invention.

The present invention also relates to a detergent composition comprising an endoglucanase variant of the invention, optionally in combination with one or several additional enzymes such as amylases, mannases, cellulases, lipases, pectinases, proteases, endoglucanases, and/or exoglucanases. Detergent compositions of the present invention are in any convenient form (e.g., a bar, a tablet, a powder, a granule, a paste or a liquid). Detergent compositions may comprise one or more surfactant, typically at a level of from 0.1% to 60% by weight.

In a last aspect, the present invention relates to the use of an endoglucanase variant, a composition or a host cell of the invention for paper pulp bleaching. The present invention also relates to a method of bleaching paper pulp comprising contacting the paper pulp with an endoglucanase variant, a composition or a host cell of the invention. The variant of the invention may be used in combination with one or several additional enzymes such as xylanase, endoglucanase, alpha-galactosidase and/or cellobiohydrolase enzymes.

Further aspects and advantages of the present invention will be described in the following examples, which should be regarded as illustrative and not limiting.

EXAMPLES

Materials and Methods

Cloning of the Egl1 cDNA:

The cDNA sequence corresponding to the precursor of *Trichoderma reesei* endoglucanase I (Swiss-Prot P07981, including the signal sequence; SEQ ID NO:1) was cloned in the expression vector pYes2 (Invitrogen) under the control of the inducible GAL1 promotor. The vector was used to transform the *Saccharomyces cerevisiae* strain BY4247 (MATα his3Δ leu2Δ lysΔ ura3Δ) by electroporation (7.5 kV/cm) using a MicroPulser Electroporation Apparatus (BioRad). The colonies were spread on SD-U agar plates (SD-Agar 46.7 g/L, Fluka 84605; Csm-Ura 0.77 g/L, MPBiomedicals 114511-222) and incubated 72 h at 30° C.

DNA sequences encoding endoglucanase I variants of the present invention (E117K, D241 G, T7I, M91L, E117K+D241G, E117K+D241G+T7I, E117K+D241G+T7I+M91L) were obtained from this construction using the Biométhodes' proprietary technology Massive Mutagenesis® described in the U.S. Pat. No. 7,202,086 or in Saboulard et al, 2005. The variant E117K+D241G+T7I without CBM domain was obtained by substituting the alanine 397 of the SEQ ID NO: 1 by a STOP codon using overlapped PCRs.

Preparation of Substrates:

Preparation of the Phosphoric Acid Swollen Cellulose (PASC) 1%:

PASC was prepared as already described by Den Haan et al. (2007). The PASC was finally resuspended in a final volume of 200 mL (to be at 1%) or in a final volume of 800 mL (to be at 0.25%) with sodium acetate 50 mM pH4, pH5 or pH6. The pH was checked and adjusted to pH4, 5 or 6, if needed.

Preparation of Xylan 0.25%:

One g of xylan from beechwood (Sigma X4252) was mixed in 400 ml of sodium acetate buffer 50 mM pH4, pH5 or pH6. The mix was heated under agitation until boiling was reached. The heating was then stopped and slight agitation was maintained overnight.

Time Curve of Cellulase Activity on PASC:

Production of the Enzyme:

One colony of yeast transformed with the expression vector pYes2 comprising the gene encoding wild-type *T. reesei* endoglucanase I or a variant according to the invention was picked and used to inoculate 5 mL of SD-U liquid medium (DOB 27 g/L, MPBiomedicals 114025-022; Csm-Ura 0.77 g/L, MPBiomedicals 114511-222). The preculture was incubated at 30° C. for 24 h under agitation (250 rpm). After measurement of the $OD_{600}$, the preculture was used to inoculate a 50 mL culture of YPSuccGal (Bacto Yeast Extract 10 g/L, Difco 217750; BactoTryptone 20 g/L, Difco 211705; Succinic acid 17.7 g/L, the pH of the culture medium was adjusted at pH5.5 with NaOH 10N, and supplemented with galactose at 2% final concentration) at 0.5 $uOD_{600}$/mL. After an incubation of 48 h at 30° C. under agitation (250 rpm), the culture was centrifuged 5 min at 4000 rpm and the supernatant was recovered and concentrated to 1 mL using Vivaspin20 30000MWCO (Sartorius VS2022).

Figure 2:
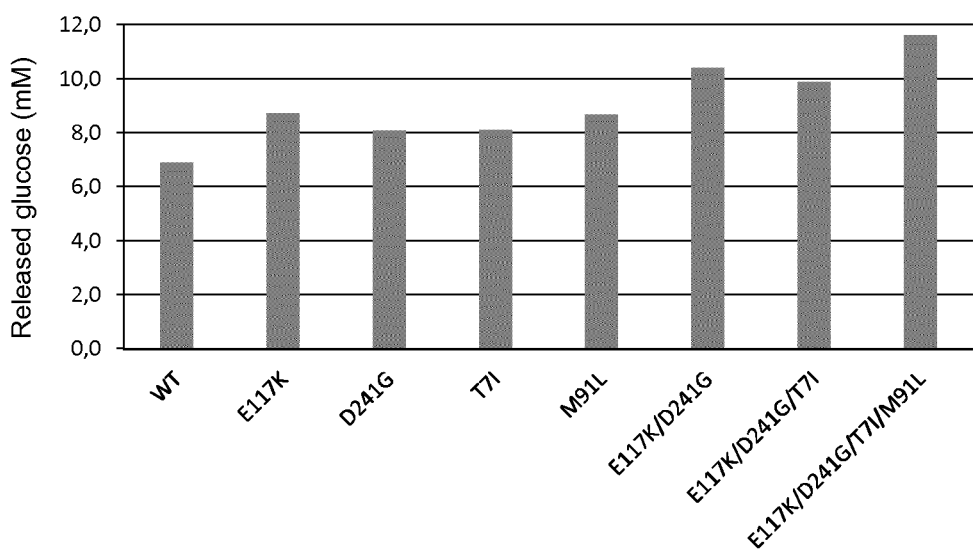
FIG. 2: Cellulase activity on PASC at 50° C. pH 5 of wild-type *T. reesei* endoglucanase I and endoglucanase variants according to the invention (E117K, D241G, T7I, M91L, E117K+D241G, E117K+D241G+T7I and E117K+D241G+T7I+M91L). Released glucose was quantified at t=24 h.
Figure 3:
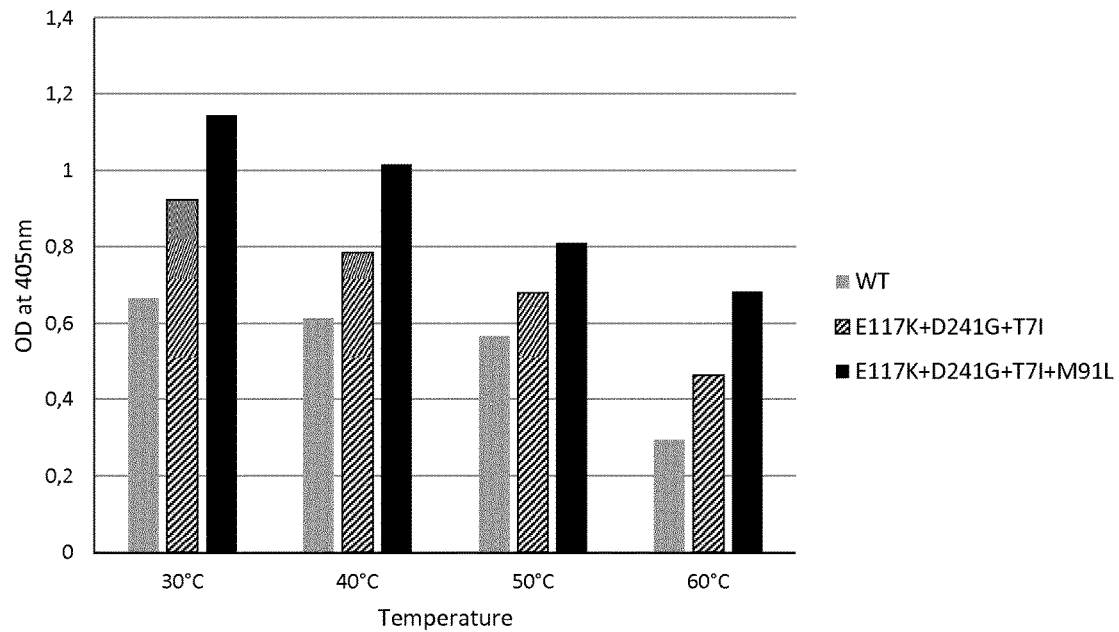
FIG. 3: Cellulase activity on PASC at 30, 40, 50 or 60° C. pH 5 of wild-type *T. reesei* endoglucanase I and endoglucanase variants according to the invention (E117K+D241G+T7I and E117K+D241G+T7I+M91L). Released glucose was quantified at t=17 h.
Figure 4:
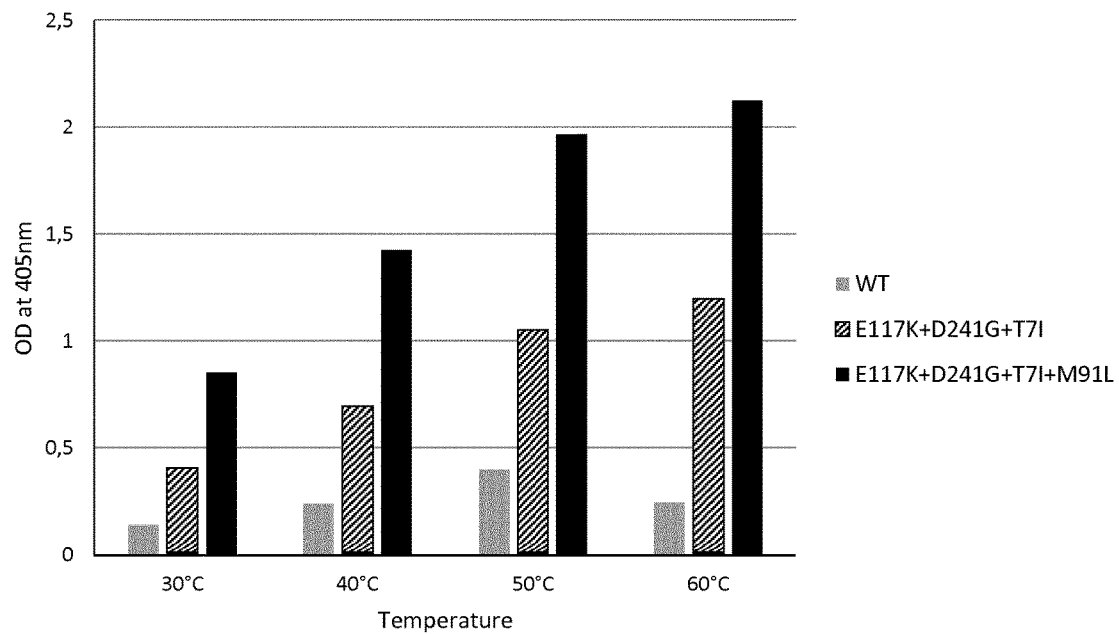
FIG. 4: Xylanase activity at 30, 40, 50 or 60° C. pH 5 of wild-type *T. reesei* endoglucanase I and endoglucanase variants according to the invention (E117K+D241G+T7I and E117K+D241G+T7I+M91L). Released glucose was quantified at t=17 h.
Figure 5:
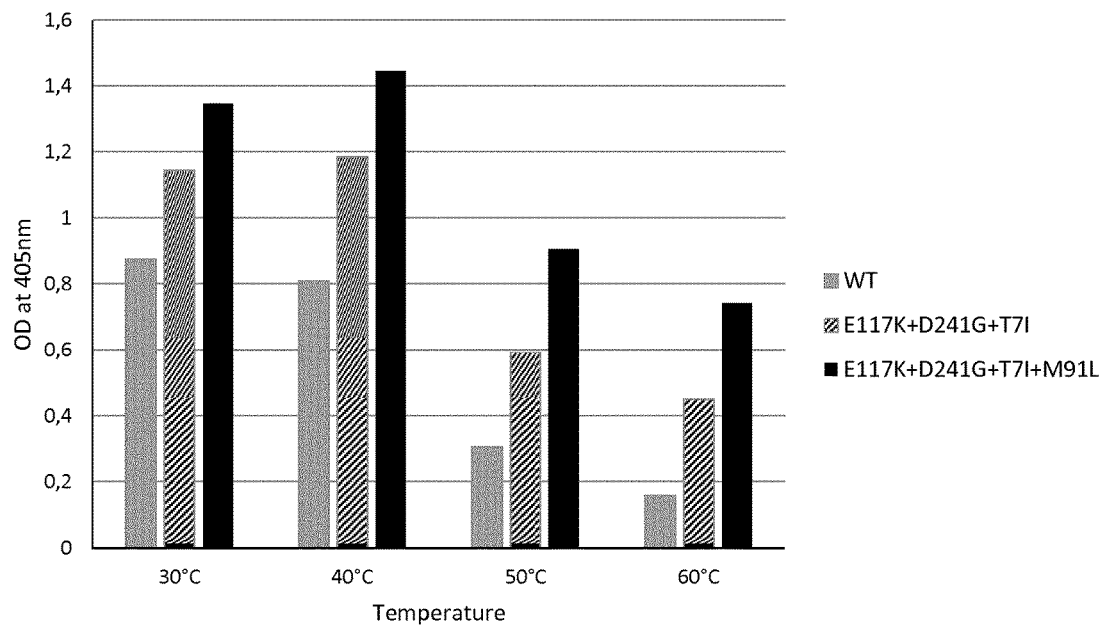
FIG. 5: Cellulase activity on PASC at 30, 40, 50 or 60° C. pH 6 of wild-type *T. reesei* endoglucanase I and endoglucanase variants according to the invention (E117K+D241G+T7I and E117K+D241G+T7I+M91L). Released glucose was quantified at t=17 h.
Figure 6:
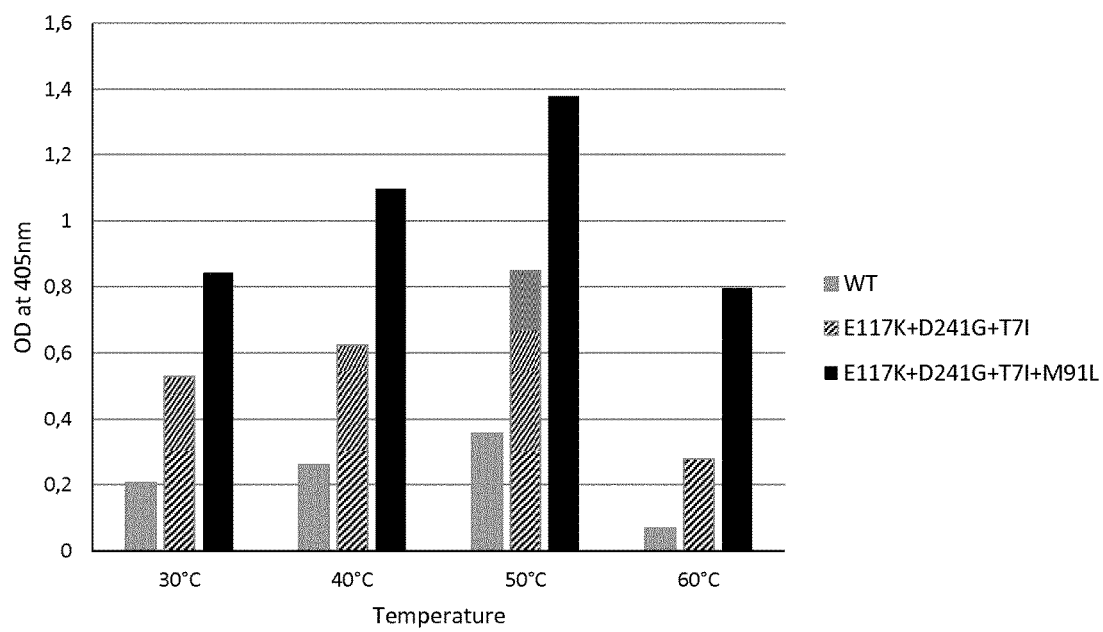
FIG. 6: Xylanase activity at 30, 40, 50 or 60° C. pH 6 of wild-type *T. reesei* endoglucanase I and endoglucanase variants according to the invention (E117K+D241G+T7I and E117K+D241G+T7I+M91L). Released glucose was quantified at t=17 h.

Activity Assay (cf. FIGS. 1 and 2):

Five mL of PASC 1% pH 5 or 6 were incubated in a 50 mL tube at 50° C. or 30° C., in the presence of 50 µl of concentrated supernatant and 45 u/g cellulose of beta-glucosidase (Cellobiase from *Aspergillus niger*, Sigma C6105). The reaction was carried out under agitation (180 rpm). At different times (from t0 to t24 h), 100 µL were taken, centrifuged 5 min at 14000 rpm, and the supernatant was recovered and stored at −20° C. until released sugar quantification assay. Samples were taken in duplicates.

Released sugar quantification assay was carried out in 96 well PCR microplates. Samples were diluted in 50 µL sodium acetate 50 mM pH5 or 6, and 100 µL of PAHBAH 0.5% were added to each well (PAHBAH (4-hydroxybenzhydrazide (Sigma, H9882)) 0.5% was prepared by diluting 10 times PAHBAH 5% (in HCl 0.5N) in NaOH 0.5N/EDTA 15 mM). Plates were incubated 30 min at 75° C., 100 µL of each well were transferred in an Elisa plate and the OD at 405 nm was read. Concentrations of released sugars were determined by referring to a glucose standard treated the same way as samples.

Thermoactivity Assay:

Production of the Enzyme:

One colony of yeast transformed with the expression vector pYes2 comprising the gene encoding wild-type *T. reesei* endoglucanase I or a variant according to the invention was picked and used to inoculate 5 mL of SD-U liquid medium (DOB 27 g/L, MPBiomedicals 114025-022; Csm-Ura 0.77 g/L, MPBiomedicals 114511-222). The preculture was incubated at 30° C. for 24 h under agitation (250 rpm). After measurement of the $OD_{600}$, the preculture was used to inoculate a 50 mL culture of YPSuccGal (Bacto Yeast Extract 10 g/L, Difco 217750; BactoTryptone 20 g/L, Difco 211705; Succinic acid 17.7 g/L, the pH of the culture medium was adjusted at pH5.5 with NaOH 10N, and supplemented with galactose at 2% final concentration) at 0.5 $uOD_{600}$/mL. After an incubation of 48 h at 30° C. under agitation (250 rpm), the culture was centrifuged 5 min at 4000 rpm and the supernatant was recovered.

Activity Assay (cf. FIGS. 3 to 6 and 9):

Activity assays were carried out in 96 well PCR microplates and incubated in MJResearch thermocyclers PTC-225. Fifty μL of PASC 1% pH5 or pH6 containing 45 u/g cellulose of beta-glucosidase (Cellobiase from *Aspergillus niger*, Sigma C6105), or xylan 0.25% pH5 or pH6 were incubated with 5 μL of 8-fold diluted culture supernatants for 17 h at 30, 40, 50 or 60° C. After the 17 h reaction, released sugars in each sample were immediately quantified by diluting the samples and adding 100 μL of PAHBAH 0.5% to each well (PAHBAH (4-hydroxybenzhydrazide (Sigma, H9882)) 0.5% was prepared by diluting 10 times PAHBAH 5% (in HCl 0.5N) in NaOH 0.5N/EDTA 15 mM). Plates were incubated 30 min at 75° C., 100$4$, of each well were transferred in an Elisa plate and the OD at 405 nm was read. For each incubation temperature, reaction was replicated 12 times and average of the 12 values was calculated.

Activity Assay (cf. FIG. 7):

Activity assays were carried out in 96 well PCR microplates and incubated in MJResearch thermocyclers PTC-225. Fifty μL of PASC 1% pH 4 or 5 containing 45 u/g cellulose of beta-glucosidase (Cellobiase from *Aspergillus niger*, Sigma C6105), or xylan 0.25% pH 4 or 5, were incubated with 10 μL of culture supernatants for 15 or 60 min at 30° C. or 50° C. After the reaction, released sugars in each sample were immediately quantified by adding 100 μL of PAHBAH 0.5% to each well (PAHBAH (4-hydroxybenzhydrazide (Sigma, H9882)) 0.5% was prepared by diluting 10 times PAHBAH 5% (in HCl 0.5N) in NaOH 0.5N/EDTA 15 mM). Plates were incubated 30 min at 75° C., 100 μL of each well were transferred in an Elisa plate and the OD at 405 nm was read.

Thermoresistance Assay:

Production of the Enzyme:

One colony of yeast transformed with the expression vector pYes2 comprising the gene encoding wild-type *T. reesei* endoglucanase I or a variant according to the invention was picked and used to inoculate 5 mL of SD-U liquid medium (DOB 27 g/L, MPBiomedicals 114025-022; Csm-Ura 0.77 g/L, MPBiomedicals 114511-222). The preculture was incubated at 30° C. for 24 h under agitation (250 rpm). After measurement of the $OD_{600}$, the preculture was used to inoculate a 50 mL culture of SC-USuccGal (YNB 5.7 g/L, MPBiomedicals 114027-812; Csm-Ura 0.77 g/L, MPBiomedicals 114511-222; NaCl 0.1 g/L; KH2PO4 1 g/L; Succinic acid 17.7 g/L, the pH of the culture medium was adjusted at pH5.5 with NaOH 10N, and supplemented with galactose at 2% final concentration) at 0.5 $uOD_{600}$/mL. After an incubation of 72 h at 30° C. under agitation (250 rpm), the culture was centrifuged 5 min at 4000 rpm and the supernatant was recovered.

Figure 8:
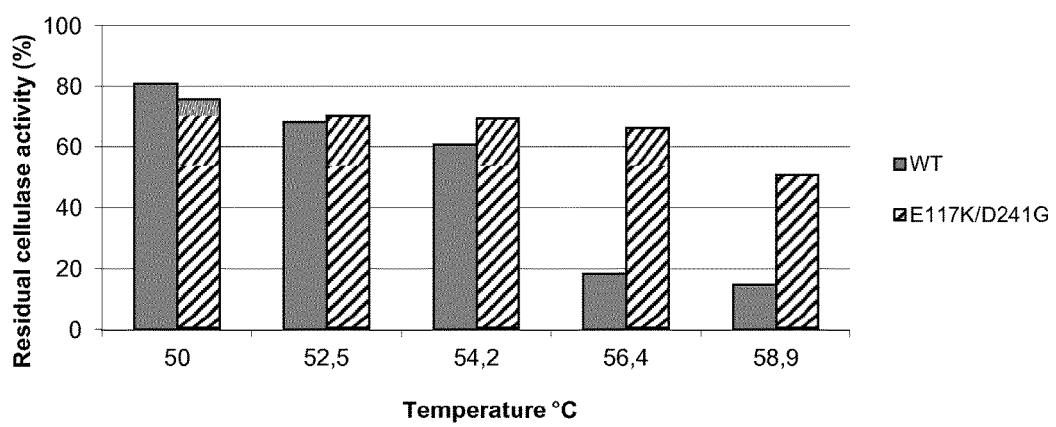
FIG. 8: Residual cellulase activity after incubation at different temperatures (from 50 to 58.9° C.) during one hour. Cellulase activity was measured at 50° C. during 30 min. Results are expressed as percentage of cellulase activity without preliminary incubation.

Activity Assay (Cf. FIG. 8):

Thirty μL of supernatant were incubated 1 h in a 96 well PCR microplate at 50, 52.5, 54.2, 56.4 and 58.9° C. using a MJResearch thermocyler PTC-225. Pre-heated supernatants were cooled in ice and 10 μL were incubated with 50 μL of PASC 1% pH 5 for 30 min at 50° C. Released sugars in each sample were immediately quantified by adding 100 μL of PAHBAH 0.5% to each well (PAHBAH (4-hydroxybenzhydrazide (Sigma, H9882)) 0.5% was prepared by diluting 10 times PAHBAH 5% (in HCl 0.5N) in NaOH 0.5N/EDTA 15 mM). Plates were incubated 30 min at 75° C., 100 μL of each well were transferred in an Elisa plate and the OD at 405 nm was read.

Results pYes2 expression vectors comprising a DNA sequence encoding wild-type (wt) *T. reesei* endoglucanase I or a variant according to the invention were transformed into the yeast *Saccharomyces cerevisiae* to be individually expressed.

Cellulase and xylanase activities were assessed for wild-type EG-I (SEQ ID NO: 2) and each variant at different temperatures and pH. In particular, these activities were assessed at 30° C. and pH6, i.e. conditions suitable for SSF or CBP process. As endoglucanases are involved in the hydrolysis of lignocellulo sic material and are usually part of commercial enzyme cocktails used at 50° C. and pH5, cellulase and xylanase activities of enzymes (wt and variants) were also assessed at 50° C. and pH5.

The cellulase activity was assessed at 30° C. and pH6 (FIG. 1) and at 50° C. and pH5 (FIG. 2) for the wt enzyme and variants comprising one, two, three or four substitutions (E117K, D241G, T7I, M91L, E117K+D241G, E117K+D241G+T7I and E117K+D241G+T7I+M91L). The xylanase activity was also assessed at 30° C. and pH6 (FIG. 3) and at 50° C. and pH5 (FIG. 4) for the wt enzyme and these variants.

The ratio between the concentration of glucose released by a variant to the one released by the WT enzyme represents the improvement factor. This improvement factor can be calculated for each variant at each hydrolysis condition (Table 1).

TABLE 1

| Improvement factor of each variant at 30° C.—pH6 or 50° C.—pH5 | | | | | | | |
|---|---|---|---|---|---|---|---|
| | WT | E117K | D241G | T7I | M91L | E117K/ D241G | E117K/ D241G/T7I | E117K/ D241G/T7I/ M91L |
| 30° C.—pH6 | 1 | 1.53 | 1.46 | 1.36 | 1.22 | 1.51 | 1.56 | 2.36 |
| 50° C.—pH5 | 1 | 1.26 | 1.17 | 1.17 | 1.26 | 1.51 | 1.43 | 1.68 |

It appears that all single and multiple variants show an increased cellulase activity at 30° C.-pH6 and 50° C.-pH5 regarding the wt enzyme EG-I. In particular, these results show that the cellulase activity at 30° C.-pH6 of the quadruple variant (E117K+D241G+T7I+M91L) is dramatically increased.

With the goal to show that the activities of variants were improved regarding the wt enzyme on a large range of conditions, cellulase (FIG. 5) and xylanase (FIG. 6) activities were assessed at pH6 and at different temperatures (from 30° C. to 60° C.). Results show that whatever the conditions tested, the cellulase and xylanase activities of variants were significantly improved regarding the wt enzyme.

Figure 7:
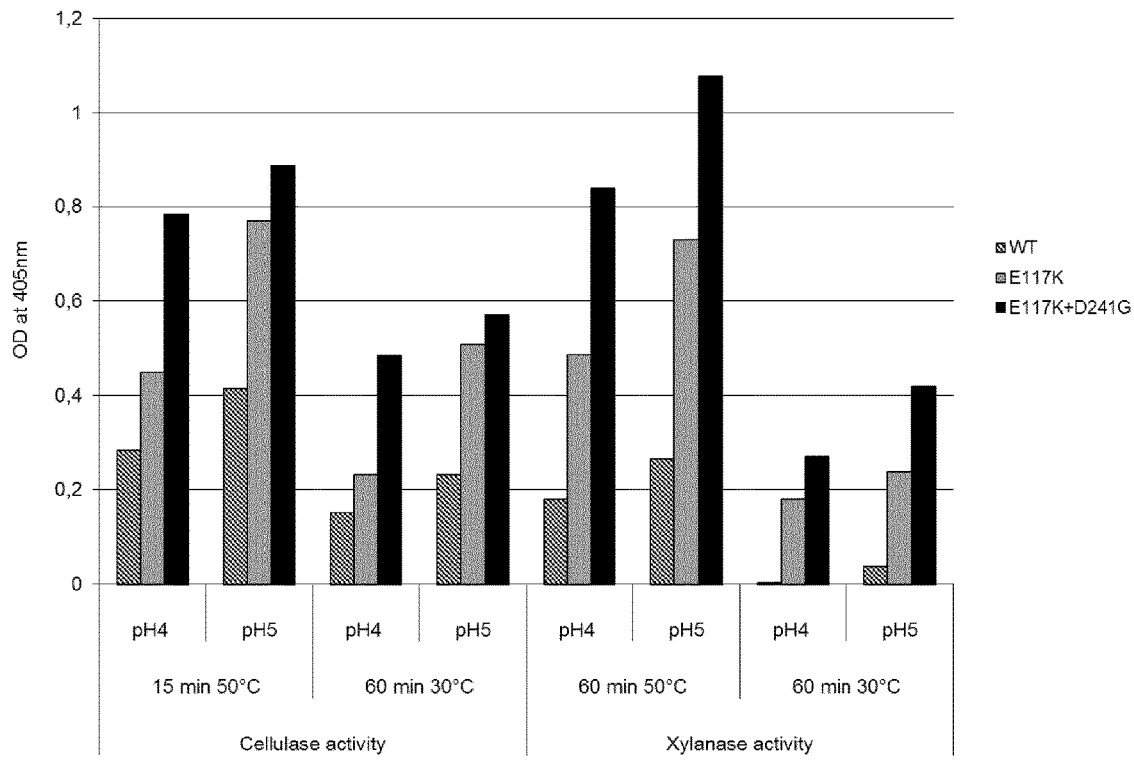
FIG. 7: Cellulase and xylanase activities at 30 or 50° C. and pH 4 or 5 of wild-type *T. reesei* endoglucanase I and endoglucanase variants according to the invention (E117K and E117K+D241G). Released glucose was quantified at t=15 or 60 min.

Moreover, FIG. 7 shows that the substitution E117K alone or in combination with the substitution D241G imparts to the enzyme a significant improvement for cellulase and xylanase activities at pH 4, whatever the incubation temperature, 30° C. or 50° C.

These results thus demonstrate that the variants of the invention can then be used with great interest in a large range of processes for hydrolysis, associated or not to fermentation, of cellulose and hemicellulose substrates.

The inventors also determined the thermoresistance of an exemplary variant, i.e. E117K+D241G (FIG. 8). For this, the supernatants containing either the wt enzyme or the variant E117K+D241G were incubated for 1 h at several temperatures. The cellulase activity was then measured (at 50° C. and pH5 during 30 min) and the residual activity was determined by calculating the ratio between this activity and those obtained without preliminary incubation. Results presented on FIG. 8 demonstrate that the variant exhibits an improved thermoresistance. In particular, after a pre-incubation of 1 h at 58.9° C., the variant still exhibits more than 50% of residual activity while the wt enzyme has no more than 15% of residual activity.

Figure 9:
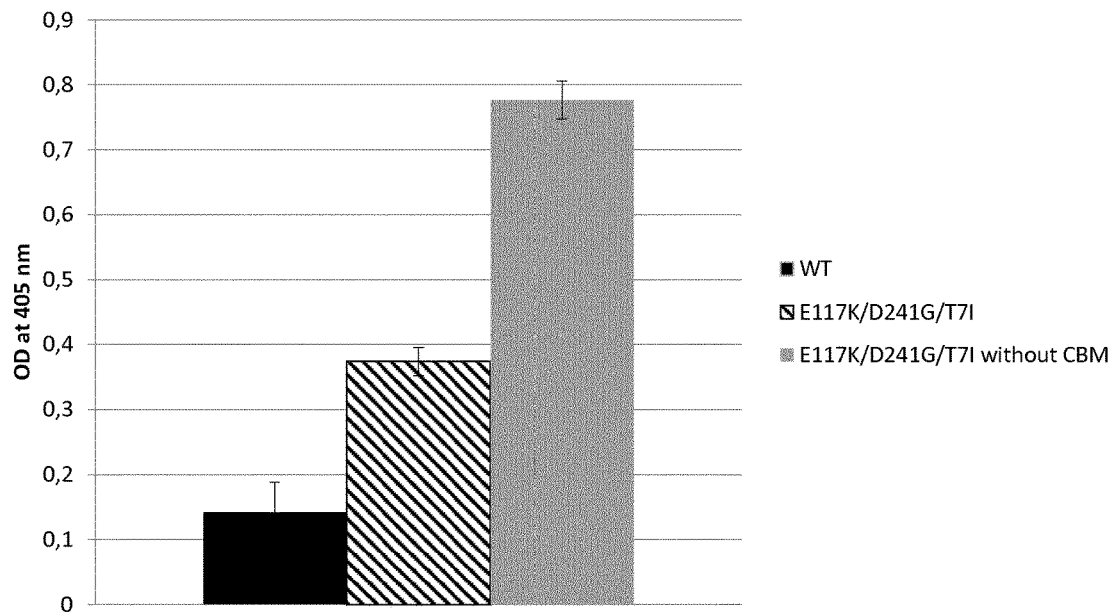
FIG. 9: Cellulase activity on PASC at 30° C. pH 6 of wild-type *T. reesei* endoglucanase I and endoglucanase variants according to the invention (E117K+D241G+T7I (with CBM) and E117K+D241G+T7I without CBM). Released glucose was quantified at t=17 h.
Figure 10:
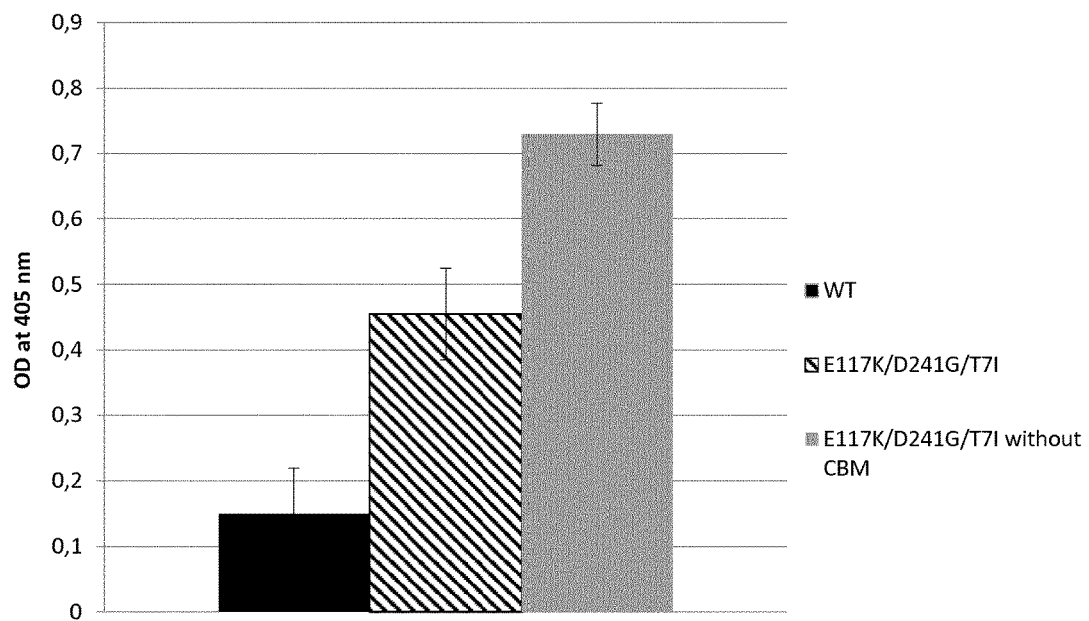
FIG. 10: Xylanase activity at 30° C. pH 6 of wild-type *T. reesei* endoglucanase I and endoglucanase variants according to the invention (E117K+D241G+T7I (with CBM) and E117K+D241G+T7I without CBM). Released glucose was quantified at t=17 h.

The wt enzyme EG-I (SEQ ID NO: 2) has a linker and a cellulose binding domain (CBM) at its C-terminal extremity. A STOP mutation was introduced between the catalytic core of the enzyme and the linker+ CBM domain (i.e. at position 397 of the SEQ ID NO: 1) to determine if the variants of the invention keep their efficiency without the CBM structure. FIGS. 9 and 10 show that the E117K/D241G/T7I variant lacking the CBM structure exhibits strong cellulase and xylanase activities. The difference between this variant and a variant comprising the same substitutions and a CBM domain is likely from a better expression of the enzyme rather than from a better specific activity of the variant without CBM domain. The CBM is supposed to promote the adsorption of the enzyme on the cellulose fibrils and to direct these fibrils towards the active site. One can suppose that this role is more important for cellobiohydrolases, which have a tunnel form active site, than for T. reesei EG-I whose active site is more open, with a groove form.

REFERENCES

Agaisse and Lereclus, 1994, Molecular Microbiology 13: 97-107
Ballesteros et al. (2004) Process Biochem. 39(12), 1843-1848
Cooper et al., 1993, EMBO J. 12: 2575-2583
Cullen et al., 1987, Nucleic Acids Res. 15: 9163-9175
Dawson et al., 1994, Science 266: 776-779
DeBoer et al., 1983, Proc. Natl. Acad. Sci. USA 80: 21-25
Den Haan et al (2007) Metab Eng. January; 9(1):87-94.
Dienes et al. (2006) Process Biochem, 41(9), 2092-2096
Egon et al., 1988, Gene 69: 301-315
Hari Krishna et al. (2000) J. Agric. Food Chem. 48, 1971-1976
Altschul et al (1997) Nucleic Acids Res. 25:3389-3402.
Altschul et al (2005) FEBS J. 272:5101-5109
Gems et al., 1991, Gene 98: 61-67
Ghose. Pure Appl Chem, 1987; 59:257-68.
Gilbert et al., 1980, Scientific American 242: 74-94
Guo and Sherman, 1995, Mol. Cellular Biol. 15: 5983-5990
Hawksworth et al., In, Ainsworth and Bisby's Dictionary of The Fungi, 8th edition, 1995, CAB International, University Press, Cambridge, UK
Hong et al. (2007) Journal of Biotechnology, 130, 114-123
Hue et ai, 1995, Journal of Bacteriology 177: 3465-3471
Kadam et al. (1997) Appl. Microbiol. Biotechnol. 48(6), 709-713
Kidby and Davidson. Anal Biochem 1973; 55:321-5.
Kuhls et al (1996) Proc. Natl. Acad. Sci. U.S.A. 93 (15): 7755-7760.
Nakazawa et al. Appl Microbiol Biotechnol. 2008 December; 81(4):681-9.
Lever et al. J Lab Clin Med 1973; 82:649-55.
Needleman & Wunsch, J. Mol. Biol 48:443, 1970
Nelson J Biol Chem 1944; 153:375-80.
Roe. J Biol Chem 1955; 212:335-43.
Romanos et al., 1992, Yeast 8: 423-488.
Saboulard et al, 2005 Biotechniques, 2005 September 39(3): 363-8
Saha et al. (2005) Process Biochemistry 40, 3693-3700
Sambrook J, Russell D (2001) Molecular cloning: a laboratory manual, Third
Edition Cold Spring Harbor
Simonen and Palva, 1993, Microbiological Reviews 57: 109-137
Smith & Waterman, Adv. Appl. Math. 2:482, 1981
Villa-Kamaroff et al., 1978, Proc. Natl. Acad. Sci. USA 75: 3727-3731
Zhang et al., 2006, Biotechnology Advances 24: 452-481
Zhang and Lynd. Appl Environ Microbiol 2004; 70:1563-9.
Zhang and Lynd. Biomacromolecules 2005; 6:1510-5.

The invention claimed is:

1. An endoglucanase I variant comprising a sequence (i) having at least 96% identity to the full length amino acid sequence set forth in SEQ ID NO: 3 and (ii) comprising at least one substitution at position corresponding to residue E117, D241, T7 or M91 of SEQ ID NO: 3, wherein said variant exhibits an improved cellulase and/or xylanase activity compared to *Trichoderma reesei* endoglucanase I of SEQ ID NO: 2.

2. The variant according to claim 1, wherein said variant comprises at least two substitutions at positions corresponding to residues selected from the group consisting of E117, D241, T7 and M91 of SEQ ID NO: 3.

3. The variant according to claim 1, wherein said variant comprises substitutions at positions corresponding to residues E117 and D241.

4. The variant according to claim 1, wherein said variant comprises at least three substitutions at positions corresponding to residues selected from the group consisting of E117, D241, T7 and M91 of SEQ ID NO: 3.

5. The variant according to claim 1, wherein said variant comprises substitutions at positions corresponding to residues E117, D241, T7 and M91 of SEQ ID NO: 3.

6. The variant according to claim 1, wherein said variant comprises one or several substitutions selected from the group consisting of E117K, D241G, T7I and M91L.

7. The variant according to claim 1, wherein said variant comprises substitutions at positions corresponding to residues E117, D241, T7 and M91 of SEQ ID NO: 3 and wherein said substitutions are E117K, D241G, T7I and M91L.

8. The variant according to claim 1, wherein said variant lacks carbohydrate-binding module (CBM) domain.

9. A nucleic acid encoding a variant as defined in claim 1.

10. An expression cassette or vector comprising the nucleic acid of claim 9.

11. A host cell comprising the nucleic acid of claim 9.

12. A method of producing an endoglucanase 1 variant comprising:
    (a) culturing the host cell according to claim 11 in a suitable culture medium under suitable conditions to produce endoglucanase I variant; and
    (b) recovering said variant from the cell culture.

13. A method of converting cellulosic biomass to monomeric sugars comprising contacting the biomass with the endoglucanase I variant of claim 1.

14. A method of producing a fermentation product from cellulosic biomass comprising:
    (a) contacting the biomass with the endoglucanase I variant according to claim 1 thereby degrading the biomass into monomeric sugars; and
    (b) fermenting monomeric sugars obtained in step (a) into said fermentation product.

15. The method according to claim 14, wherein steps (a) and (b) are conducted at the same temperature and/or the same pH.

16. A host cell comprising the expression cassette or vector of claim 10.

17. A method of producing a fermentation product from cellulosic biomass comprising:
    (a) contacting the biomass with the host cell of claim 11 thereby degrading the biomass into monomeric sugars; and
    (b) fermenting monomeric sugars obtained in step (a) into said fermentation product.

18. The method according to claim 17, wherein steps (a) and (b) are conducted at the same temperature and/or the same pH.

19. The method according to claim 18, wherein steps (a) and (b) are conducted at 30° C. and/or pH 6.

20. A method of converting cellulosic biomass to monomeric sugars comprising contacting the biomass with the host cell according to claim 11.

* * * * *

SEQUENCE LISTING

```
<160> NUMBER OF SEQ ID NOS: 3

<210> SEQ ID NO 1
<211> LENGTH: 459
<212> TYPE: PRT
<213> ORGANISM: Trichoderma reesei

<400> SEQUENCE: 1

Met Ala Pro Ser Val Thr Leu Pro Leu Thr Thr Ala Ile Leu Ala Ile
1               5                   10                  15

Ala Arg Leu Val Ala Ala Gln Gln Pro Gly Thr Ser Thr Pro Glu Val
            20                  25                  30

His Pro Lys Leu Thr Thr Tyr Lys Cys Thr Lys Ser Gly Gly Cys Val
        35                  40                  45

Ala Gln Asp Thr Ser Val Val Leu Asp Trp Asn Tyr Arg Trp Met His
    50                  55                  60

Asp Ala Asn Tyr Asn Ser Cys Thr Val Asn Gly Gly Val Asn Thr Thr
```

```
            65                  70                  75                  80

Leu Cys Pro Asp Glu Ala Thr Cys Gly Lys Asn Cys Phe Ile Glu Gly
                    85                  90                  95

Val Asp Tyr Ala Ala Ser Gly Val Thr Thr Ser Gly Ser Ser Leu Thr
                100                 105                 110

Met Asn Gln Tyr Met Pro Ser Ser Gly Gly Tyr Ser Ser Val Ser
            115                 120                 125

Pro Arg Leu Tyr Leu Leu Asp Ser Asp Gly Glu Tyr Val Met Leu Lys
        130                 135                 140

Leu Asn Gly Gln Glu Leu Ser Phe Asp Val Asp Leu Ser Ala Leu Pro
145                 150                 155                 160

Cys Gly Glu Asn Gly Ser Leu Tyr Leu Ser Gln Met Asp Glu Asn Gly
                165                 170                 175

Gly Ala Asn Gln Tyr Asn Thr Ala Gly Ala Asn Tyr Gly Ser Gly Tyr
                180                 185                 190

Cys Asp Ala Gln Cys Pro Val Gln Thr Trp Arg Asn Gly Thr Leu Asn
            195                 200                 205

Thr Ser His Gln Gly Phe Cys Cys Asn Glu Met Asp Ile Leu Glu Gly
        210                 215                 220

Asn Ser Arg Ala Asn Ala Leu Thr Pro His Ser Cys Thr Ala Thr Ala
225                 230                 235                 240

Cys Asp Ser Ala Gly Cys Gly Phe Asn Pro Tyr Gly Ser Gly Tyr Lys
                245                 250                 255

Ser Tyr Tyr Gly Pro Gly Asp Thr Val Asp Thr Ser Lys Thr Phe Thr
                260                 265                 270

Ile Ile Thr Gln Phe Asn Thr Asp Asn Gly Ser Pro Ser Gly Asn Leu
            275                 280                 285

Val Ser Ile Thr Arg Lys Tyr Gln Gln Asn Gly Val Asp Ile Pro Ser
        290                 295                 300

Ala Gln Pro Gly Gly Asp Thr Ile Ser Ser Cys Pro Ser Ala Ser Ala
305                 310                 315                 320

Tyr Gly Gly Leu Ala Thr Met Gly Lys Ala Leu Ser Ser Gly Met Val
                325                 330                 335

Leu Val Phe Ser Ile Trp Asn Asp Asn Ser Gln Tyr Met Asn Trp Leu
            340                 345                 350

Asp Ser Gly Asn Ala Gly Pro Cys Ser Ser Thr Glu Gly Asn Pro Ser
        355                 360                 365

Asn Ile Leu Ala Asn Asn Pro Asn Thr His Val Val Phe Ser Asn Ile
        370                 375                 380

Arg Trp Gly Asp Ile Gly Ser Thr Thr Asn Ser Thr Ala Pro Pro Pro
385                 390                 395                 400

Pro Pro Ala Ser Ser Thr Thr Phe Ser Thr Thr Arg Arg Ser Ser Thr
                405                 410                 415

Thr Ser Ser Ser Pro Ser Cys Thr Gln Thr His Trp Gly Gln Cys Gly
                420                 425                 430

Gly Ile Gly Tyr Ser Gly Cys Lys Thr Cys Thr Ser Gly Thr Thr Cys
            435                 440                 445

Gln Tyr Ser Asn Asp Tyr Tyr Ser Gln Cys Leu
        450                 455

<210> SEQ ID NO 2
<211> LENGTH: 437
<212> TYPE: PRT
<213> ORGANISM: Trichoderma reesei
```

<400> SEQUENCE: 2

```
Gln Gln Pro Gly Thr Ser Thr Pro Glu Val His Pro Lys Leu Thr Thr
1               5                   10                  15

Tyr Lys Cys Thr Lys Ser Gly Gly Cys Val Ala Gln Asp Thr Ser Val
            20                  25                  30

Val Leu Asp Trp Asn Tyr Arg Trp Met His Asp Ala Asn Tyr Asn Ser
        35                  40                  45

Cys Thr Val Asn Gly Gly Val Asn Thr Thr Leu Cys Pro Asp Glu Ala
    50                  55                  60

Thr Cys Gly Lys Asn Cys Phe Ile Glu Gly Val Asp Tyr Ala Ala Ser
65                  70                  75                  80

Gly Val Thr Thr Ser Gly Ser Ser Leu Thr Met Asn Gln Tyr Met Pro
                85                  90                  95

Ser Ser Ser Gly Gly Tyr Ser Ser Val Ser Pro Arg Leu Tyr Leu Leu
                100                 105                 110

Asp Ser Asp Gly Glu Tyr Val Met Leu Lys Leu Asn Gly Gln Glu Leu
            115                 120                 125

Ser Phe Asp Val Asp Leu Ser Ala Leu Pro Cys Gly Glu Asn Gly Ser
        130                 135                 140

Leu Tyr Leu Ser Gln Met Asp Glu Asn Gly Gly Ala Asn Gln Tyr Asn
145                 150                 155                 160

Thr Ala Gly Ala Asn Tyr Gly Ser Gly Tyr Cys Asp Ala Gln Cys Pro
                165                 170                 175

Val Gln Thr Trp Arg Asn Gly Thr Leu Asn Thr Ser His Gln Gly Phe
            180                 185                 190

Cys Cys Asn Glu Met Asp Ile Leu Glu Gly Asn Ser Arg Ala Asn Ala
        195                 200                 205

Leu Thr Pro His Ser Cys Thr Ala Thr Ala Cys Asp Ser Ala Gly Cys
210                 215                 220

Gly Phe Asn Pro Tyr Gly Ser Gly Tyr Lys Ser Tyr Tyr Gly Pro Gly
225                 230                 235                 240

Asp Thr Val Asp Thr Ser Lys Thr Phe Thr Ile Ile Thr Gln Phe Asn
                245                 250                 255

Thr Asp Asn Gly Ser Pro Ser Gly Asn Leu Val Ser Ile Thr Arg Lys
            260                 265                 270

Tyr Gln Gln Asn Gly Val Asp Ile Pro Ser Ala Gln Pro Gly Gly Asp
        275                 280                 285

Thr Ile Ser Ser Cys Pro Ser Ala Ser Ala Tyr Gly Gly Leu Ala Thr
    290                 295                 300

Met Gly Lys Ala Leu Ser Ser Gly Met Val Leu Val Phe Ser Ile Trp
305                 310                 315                 320

Asn Asp Asn Ser Gln Tyr Met Asn Trp Leu Asp Ser Gly Asn Ala Gly
                325                 330                 335

Pro Cys Ser Ser Thr Glu Gly Asn Pro Ser Asn Ile Leu Ala Asn Asn
            340                 345                 350

Pro Asn Thr His Val Val Phe Ser Asn Ile Arg Trp Gly Asp Ile Gly
        355                 360                 365

Ser Thr Thr Asn Ser Thr Ala Pro Pro Pro Pro Ala Ser Ser Thr
    370                 375                 380

Thr Phe Ser Thr Thr Arg Arg Ser Ser Thr Thr Ser Ser Ser Pro Ser
385                 390                 395                 400

Cys Thr Gln Thr His Trp Gly Gln Cys Gly Gly Ile Gly Tyr Ser Gly
```

```
                    405                 410                 415
Cys Lys Thr Cys Thr Ser Gly Thr Thr Cys Gln Tyr Ser Asn Asp Tyr
            420                 425                 430

Tyr Ser Gln Cys Leu
        435

<210> SEQ ID NO 3
<211> LENGTH: 375
<212> TYPE: PRT
<213> ORGANISM: Trichoderma reesei

<400> SEQUENCE: 3

Gln Gln Pro Gly Thr Ser Thr Pro Glu Val His Pro Lys Leu Thr Thr
1               5                   10                  15

Tyr Lys Cys Thr Lys Ser Gly Gly Cys Val Ala Gln Asp Thr Ser Val
            20                  25                  30

Val Leu Asp Trp Asn Tyr Arg Trp Met His Asp Ala Asn Tyr Asn Ser
        35                  40                  45

Cys Thr Val Asn Gly Gly Val Asn Thr Thr Leu Cys Pro Asp Glu Ala
    50                  55                  60

Thr Cys Gly Lys Asn Cys Phe Ile Glu Gly Val Asp Tyr Ala Ala Ser
65                  70                  75                  80

Gly Val Thr Thr Ser Gly Ser Ser Leu Thr Met Asn Gln Tyr Met Pro
                85                  90                  95

Ser Ser Ser Gly Gly Tyr Ser Ser Val Ser Pro Arg Leu Tyr Leu Leu
            100                 105                 110

Asp Ser Asp Gly Glu Tyr Val Met Leu Lys Leu Asn Gly Gln Glu Leu
        115                 120                 125

Ser Phe Asp Val Asp Leu Ser Ala Leu Pro Cys Gly Glu Asn Gly Ser
    130                 135                 140

Leu Tyr Leu Ser Gln Met Asp Glu Asn Gly Gly Ala Asn Gln Tyr Asn
145                 150                 155                 160

Thr Ala Gly Ala Asn Tyr Gly Ser Gly Tyr Cys Asp Ala Gln Cys Pro
                165                 170                 175

Val Gln Thr Trp Arg Asn Gly Thr Leu Asn Thr Ser His Gln Gly Phe
            180                 185                 190

Cys Cys Asn Glu Met Asp Ile Leu Glu Gly Asn Ser Arg Ala Asn Ala
        195                 200                 205

Leu Thr Pro His Ser Cys Thr Ala Thr Ala Cys Asp Ser Ala Gly Cys
    210                 215                 220

Gly Phe Asn Pro Tyr Gly Ser Gly Tyr Lys Ser Tyr Tyr Gly Pro Gly
225                 230                 235                 240

Asp Thr Val Asp Thr Ser Lys Thr Phe Thr Ile Ile Thr Gln Phe Asn
                245                 250                 255

Thr Asp Asn Gly Ser Pro Ser Gly Asn Leu Val Ser Ile Thr Arg Lys
            260                 265                 270

Tyr Gln Gln Asn Gly Val Asp Ile Pro Ser Ala Gln Pro Gly Gly Asp
        275                 280                 285

Thr Ile Ser Ser Cys Pro Ser Ala Ser Ala Tyr Gly Gly Leu Ala Thr
    290                 295                 300

Met Gly Lys Ala Leu Ser Ser Gly Met Val Leu Val Phe Ser Ile Trp
305                 310                 315                 320

Asn Asp Asn Ser Gln Tyr Met Asn Trp Leu Asp Ser Gly Asn Ala Gly
                325                 330                 335
```

```
Pro Cys Ser Ser Thr Glu Gly Asn Pro Ser Asn Ile Leu Ala Asn Asn
            340                 345                 350

Pro Asn Thr His Val Val Phe Ser Asn Ile Arg Trp Gly Asp Ile Gly
        355                 360                 365

Ser Thr Thr Asn Ser Thr Ala
    370             375
```